(12) United States Patent
Melvin

(10) Patent No.: US 8,052,753 B2
(45) Date of Patent: Nov. 8, 2011

(54) PROSTHETIC ANCHOR AND METHOD OF MAKING SAME

(75) Inventor: David Boyd Melvin, Loveland, OH (US)

(73) Assignee: University Of Cincinnati, Cincinnati, OH (US)

( * ) Notice: Subject to any disclaimer, the term of this patent is extended or adjusted under 35 U.S.C. 154(b) by 627 days.

(21) Appl. No.: 11/813,469

(22) PCT Filed: Jan. 9, 2006

(86) PCT No.: PCT/US2006/000555
§ 371 (c)(1),
(2), (4) Date: Jul. 8, 2008

(87) PCT Pub. No.: WO2006/074413
PCT Pub. Date: Jul. 13, 2006

(65) Prior Publication Data
US 2008/0269894 A1    Oct. 30, 2008

Related U.S. Application Data

(60) Provisional application No. 60/642,016, filed on Jan. 7, 2005.

(51) Int. Cl.
*A61F 2/08* (2006.01)
(52) U.S. Cl. .................. 623/13.14; 623/13.11; 623/13.2
(58) Field of Classification Search ............... 623/13.11, 623/13.14, 13.17, 13.18, 13.2, 14.12, 15.11, 623/23.51; 604/399; 606/232, 187, 286
See application file for complete search history.

(56) References Cited

U.S. PATENT DOCUMENTS

| 3,595,230 | A | 7/1971 | Suyeoka |
| 3,725,984 | A | 4/1973 | Graber |
| 4,149,277 | A | 4/1979 | Bokros |
| 4,187,558 | A | 2/1980 | Dahlen |
| 4,255,820 | A | 3/1981 | Rothermel |
| 4,345,601 | A | 8/1982 | Fukuda |
| 4,366,459 | A | 12/1982 | Vitola |

(Continued)

FOREIGN PATENT DOCUMENTS

EP    0780107    6/1997

(Continued)

OTHER PUBLICATIONS

Farrar, et al. (1992), "A New Skeletal Linear-pull Energy Convertor as a Power Source for Prosthetic Circulatory Support Devices", Journal of Heart and Lung Transplantation, pp. S341-S349.

(Continued)

*Primary Examiner* — Alvin Stewart
*Assistant Examiner* — Yashita Sharma

(57) ABSTRACT

The present invention is directed towards a prosthetic anchor (36) including a central layer (1) through which embedded fibers (2), such as artificial tendons, pass in defined pathways (4), a 'deep' surface membrane (7) which interfaces with a hard structure, whether that is a prosthesis, a bone, or other hard tissue, and a 'superficial' surface membrane (8) which interfaces adjacent tissue and may be configured to adhere or not to adhere to that tissue. The central layer (1) is positioned intermediate the surface membranes (7, 8) which are mechanically and/or adherently attached thereto. Also, non-limiting examples of methods of fabrication and of affixing the anchor (36) to a relatively rigid structure, natural or prosthetic, in a human or animal body with improved stress distribution in the fixed tension member end are taught.

17 Claims, 20 Drawing Sheets

U.S. PATENT DOCUMENTS

| | | | |
|---|---|---|---|
| 4,453,537 A | 6/1984 | Spitzer |
| 4,519,392 A | 5/1985 | Lingua |
| 4,585,458 A | 4/1986 | Kurland |
| 4,597,766 A | 7/1986 | Hilal |
| 4,662,886 A | 5/1987 | Moorse |
| 4,713,075 A | 12/1987 | Kurland |
| 4,773,910 A | 9/1988 | Chen et al. |
| 4,790,850 A | 12/1988 | Dunn et al. |
| 4,792,336 A | 12/1988 | Hlavacek et al. |
| 4,846,831 A | 7/1989 | Skillin |
| 4,917,700 A | 4/1990 | Aikins |
| 4,946,377 A | 8/1990 | Kovach |
| 4,964,414 A | 10/1990 | Handa et al. |
| 5,007,920 A | 4/1991 | Torre |
| 5,013,304 A | 5/1991 | Russell et al. |
| 5,049,155 A | 9/1991 | Bruchman et al. |
| 5,061,283 A | 10/1991 | Silvestrini |
| 5,116,372 A | 5/1992 | Laboureau |
| 5,197,983 A | 3/1993 | Berman et al. |
| 5,217,495 A | 6/1993 | Kaplan et al. |
| 5,263,984 A | 11/1993 | Li |
| 5,366,459 A | 11/1994 | Yoon |
| 5,409,499 A | 4/1995 | Yi |
| 5,411,481 A | 5/1995 | Allen et al. |
| 5,417,683 A | 5/1995 | Shiao |
| 5,443,504 A | 8/1995 | Hill |
| 5,456,715 A | 10/1995 | Liotta |
| 5,540,705 A | 7/1996 | Meade |
| 5,584,840 A | 12/1996 | Ramsey |
| 5,620,452 A | 4/1997 | Yoon |
| 5,643,308 A | 7/1997 | Markman |
| 5,667,526 A | 9/1997 | Levin |
| 5,697,978 A | 12/1997 | Sgro |
| 5,722,981 A | 3/1998 | Stevens |
| 5,766,250 A | 6/1998 | Chervitz et al. |
| 5,797,932 A | 8/1998 | Min et al. |
| 5,846,255 A | 12/1998 | Casey |
| 5,849,019 A | 12/1998 | Yoon |
| 5,865,836 A | 2/1999 | Miller |
| 5,957,977 A | 9/1999 | Melvin |
| 5,981,827 A | 11/1999 | Devlin et al. |
| 6,159,224 A | 12/2000 | Yoon |
| 6,165,186 A | 12/2000 | Fogarty et al. |
| 6,170,415 B1 | 1/2001 | Inoue et al. |
| 6,214,047 B1 | 4/2001 | Melvin |
| 6,221,103 B1 | 4/2001 | Melvin |
| 6,299,621 B1 | 10/2001 | Fogarty et al. |
| 6,312,445 B1 | 11/2001 | Fogarty et al. |
| 6,447,524 B1 | 9/2002 | Knodel et al. |
| 6,689,153 B1 | 2/2004 | Skiba |
| 6,733,510 B1 | 5/2004 | Melvin |
| 7,601,165 B2 * | 10/2009 | Stone .................. 606/232 |
| 2003/0236575 A1 * | 12/2003 | Yu et al. .................. 623/32 |
| 2007/0129811 A1 * | 6/2007 | Plouhar et al. .......... 623/23.75 |

FOREIGN PATENT DOCUMENTS

| | | |
|---|---|---|
| FR | 02638349 | 10/1998 |
| WO | WO2006074413 | 7/2006 |

OTHER PUBLICATIONS

Farrar, et al. (1995), "Mechanical Advantage of Skeletal Muscle as a Cardiac Assist Power Source", ASAIO Journal, pp. M481-M484.

Sasaki, et al. (1992), "A Skeletal Muscle Actuator for an Artificial Heart", ASAIO Journal, pp. M507-M511.

Acker, et al. (1987), "Skeletal Muscle as the Potential Power Source for a Cardiovascular Pump; Assessment in Vivo Science", vol. 236, pp. 324-327.

Salmons, et al. (1992), "Cardiac Assistance From Skeletal Muscle: A Critical Appraisal of the Various Approaches", British Heart Journal, vol. 68, pp. 333-338.

Ugolini (1986), "Skeletal Muscle for Artificial Heart Drive: Theory and in Vivo Experiments", Biomechanical Cardiac Assist, pp. 193-211.

Reichenbach, et al. (1997), "In Vivo Studies of an Implantable Energy Convertor for Skeletal Muscle Powered Cardiac Assist", ASAIO Journal, vol. 43, pp. M668-M672 (and Abstract).

Geddes, et al. (1991), "Power Capability of Skeletal Muscle to Pump Blood", Trans Am Soc. Artif. Intern Organs, vol. XXXVII, pp. 19-23.

Reichenbach, et al. (1994), "Characterization and Work Optimization of Skeletal Muscle as a VAD Power Source", ASAIO Journal, pp. M359-M363.

Melvin, et al. (1997), "Coupling of Skeletal Muscle to a Prosthesis for Circulatory Support", ASAIO Journal, vol. 43, pp. M434-M441.

* cited by examiner

PROSTHETIC ANCHOR AND METHOD OF MAKING SAME

RELATED APPLICATION

This application claims priority from U.S. Provisional Application Ser. No. 60/642,016 filed Jan. 7, 2005.

FIELD OF THE INVENTION

The present invention relates generally to fixation of artificial tendons, transmitting force from skeletal muscles, either to energy converters powering cardiac or other devices, or to natural or prosthetic bones, and more particularly, to a prosthetic anchor, to methods of fabrication, and to means of fixing thereof to a relatively rigid structure, natural or prosthetic, in a human or animal body with improved stress distribution in a fixed tension member, e.g. fixed fibers defining a tendon or ligament.

BACKGROUND OF THE INVENTION

Fixation of prosthetic flexible tension members, such as tendons or ligaments, to relatively rigid structures is a serious problem. A notable example is the use of artificial ligaments, such as the Leeds-Keio anterior cruciate ligament replacement in the knee. In that example, published experience with the usual means of bone fixation—drilling a hole in the tibia, inserting the ligament, and securing with a suture or pin—has included several instances of fragmentation of the polyester fibers of the prosthesis within a few months to a few years. A compression plate fixation has been used whereby tension members are cut and the end grasped between two plates, generally textured and held together by compression screws to grasp the tension member. While this allows greater control of local stress concentration than does a simple bone-hole, in theory it delivers extremely high shear stresses to the tension member locally, which may cause fatigue failure and breakage over the immense number of stress cycles expected to be required.

A knob-loop fixation device has been previously disclosed to address the stress-concentration issue, but requires a substantial thickness that may be disadvantageous. Such thickness could be problematic in some cardiac surgical, plastic and reconstructive surgical, or orthopaedic surgical devices, for example, in regions where skin is quite close to a coupled bone (e.g., the frontal bone in the case of a cosmetic surgical 'brow lift' prosthesis and the olecrenon in an orthopaedic surgical elbow prosthesis). Further, for either of these applications, for other plastic and orthopaedic surgical applications, or for some potential configurations of mechanical energy converters for cardiac power applications, the surface to which the coupler is attached may vary in its contour. Therefore a much thinner adapting terminus, which maintains sufficient flexibility to allow a finite number of size/shape models to conform to anatomy of reasonable individual variation, would be of benefit. Further, a structure with a soft flexible interface to fibers (reducing stress concentration) and yet a harder external surface (to interface with other tissues, adhering or not as desired) would also be advantageous.

Natural tendon ends, which are living tissue, have been connected to 'towel bar' fixtures on artificial bones, over which they are looped and sewn. Because of the shape of tendons—generally flattened in the plane of attachment, the axis of curvature is generally perpendicular to the surface to which they are to be attached. To avoid intolerable protrusion dimensions into surrounding tissue structures, the radius of curvature is very small. Since the compressive stress on a tension member surface, when that tension member is looped about any rod or pulley, is directly proportional to the tension applied and inversely proportional to both the radius of curvature and the projection of contact surface perpendicular to the transmitted tension, compressive forces intolerable by the tension member may be generated. An artificial force transmitting tension member, however, such as an artificial tendon, can be formed in any cross-sectional configuration. This allows the central stabilizing point to be relatively thin, flat, and oriented in the plane of the surface to which the tension member is to be attached.

In contrast to the 'towel bar' concept, the radius of curvature of the present invention may be made substantially larger with only minimal protrusion into surrounding tissue structures. In contrast to the 'knob loop' or 'tangential pulley' concept, the present invention does not require fibers to be organized into a circular cross-section, with imposition of a minimum thickness for a given number of fibers. The number of fibers still dictates the cross-sectional area of the bundle that passes through the matrix, but it can be very wide and quite thin, or any other combination of dimensions dictated by the device (e.g., a mechanical energy converter) or anatomic structure (e.g., a bone) to be joined.

SUMMARY OF THE INVENTION

The present invention provides for a prosthetic anchor including an implantable, flexible, force-transmitting fiber-based tissue coupler or central layer with fibers, and to non-limiting examples of methods of fabrication and of fixing the anchor to a relatively rigid structure, natural or prosthetic, in a human or animal body with improved stress distribution in a fixed tension member, such as fibers defining a tendon or ligament. The invention may be useful in addressing cardiac surgical, plastic and reconstructive surgical, or orthopedic surgical problems.

To this end, the prosthetic anchor defines a thin wafer-like device including a central layer that incorporates, or embeds, multiple bundles of fibers of a tension member, e.g. a natural or artificial tendon, to form a matrix. This central layer may include an elastomeric or other polymer material. The fibers are packed closely and concentric to each other, and generally in a horseshoe pattern, but permit permeation and interstitial distribution of the matrix. Opposing ends of each fiber exit generally on the same aspect or edge of the central layer and may be attached, such as to the muscle of a human or animal, by means commonly known in the art. Harder and thinner surface membranes such as carbon-fiber/epoxy or glass-fiber/epoxy or sheets of a biocompatible metal optionally cover both faces of the central layer, forming a 'sandwich' of variable flexibility. Flexibility is dependent on thickness of the overall structure and the materials chosen both for the surface membranes and the central matrix layer. Generally, regions near the center of the concentric path of fibers will not contain fibers and comprise either none of the layers (a central 'hole' or opening), or one, two, or all three layers.

The surface membranes may be variously configured as smooth or textured on the surface opposite the matrix layer, so as to purposefully encourage or discourage tissue adherence. The side of the membranes interfacing the matrix layer may or may not be roughened or textured so as to achieve mechanical bonding with the matrix layer. Alternatively, various adhesives may secure the surface membranes to the matrix layer. Since the rigid structure, whether hard tissue or rigid prosthesis, to which the prosthetic anchor is to be connected, will generally be moving relative to surrounding soft tissues, the peripheral margins of the anchor are generally tapered to a thin edge. The anchor is also adapted for mechanical fixation to the natural (e.g., bone) or prosthetic (e.g., metal plate) rigid structure and, more specifically, may be outfitted, for example, with simple holes for screws or anchors, or integrated pegs or hooks.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION OF THE INVENTION

Figure 1:
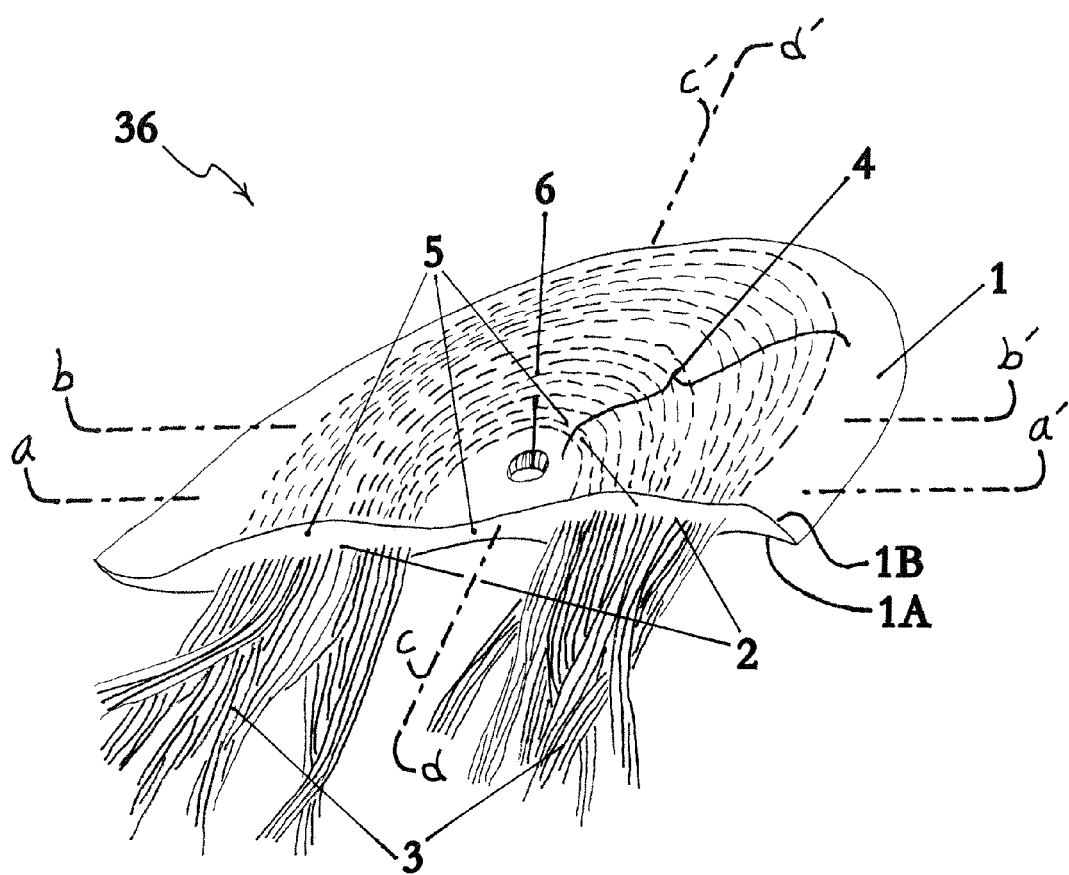
FIG. 1 is a perspective view of a central layer of the prosthetic anchor in accordance with the present invention.

Part Numbers
1. central layer; 1a. opposing first surface; 1b. opposing second surface
2. embedded fibers
3. entering and exiting fiber bundles
4. concentric pathways of fibers in central layer
5. thickened edge of central layer into which fiber bundles enter
6. optional central opening in central layer
7. deep (semi-rigid) membrane
8. superficial (semi-rigid) membrane
9. face of deep membrane configured for adherence to central layer
10. face of superficial membrane configured for adherence to central layer
11. face of deep membrane configured for adherence to a bone or to a prosthesis
12. face of superficial membrane configured for non-adherence to contiguous living tissue
13. surface, or surface replica
14. mold made to mate part 13, of a soft elastomeric material such as a polyurethane or silicone rubber. Part 14 is termed "fabrication part A" in the continuing description.
15. replica of the applicable surface of part 13, termed "fabrication part B" in description
16. clay, or clay-like moldable material, wafer configured to geometry of the device termed "fabrication part C" in description
17. hard outer cast formed to mate with the parts 15 and 16 (fabrication parts B/C assembly); that outer cast is "fabrication part D" in description
18. inner section of part 17, termed "fabrication part E" in description
19. outer section of part 17, termed "fabrication part F" in description
20. removable pin
21. smooth surface of a composite membrane
22. metal mesh insert in the deep surface of part 7, the deep membrane
23. textured metal plate insert, incorporated into the deep surface (11) of part 7, the deep membrane
24. short needle-like projections
25. peg-like central plateau
26. roughening and texturing of superficial surface (9) of the deep composite membrane (7)
27. generally parabolic disc of fabric or other porous biocompatible material
28. tows or bundles of coupler fibers
29. individual coupler fibers
30. central regions of fiber tows saturated with uncured elastomer
31. hole in disc to accommodate stabilizing pegs
32. stabilizing peg extending from either deep (shown) or superficial membrane
33. ends of tows
34. strip of uncured elastomer
35. fiber-matrix composite layup
36. prosthetic anchor
37. geometric molded or machined master replicating geometry of central layer
38. flanges to guide fiber tows 39. radial carbon or glass fibers in composite layup
40. diagonal 'a' fibers in composite layup
41. diagonal 'b' fibers in composite layup
42. fiber composite envelope
43. clasp for holding envelope during fiber insertion
44. rim joining outer and inner laminae of envelope
45. flange to hold envelope laminae apart during fiber insertion
46. bone
47. fixation screws
48. stress-distributing metal plate
49. mechanical energy converter surface to be anchored to coupled fibers by the anchor of this invention
50. frontal bone
51. olecranon of an ulna The prosthetic anchor (36) of the present invention is configured for anchoring to a hard structure such as a prosthetic device or a bone, for the goals of minimizing material stress concentration inherent to such anchoring and minimizing height of the profile of the structure beyond the surface of that hard structure.

Figure 2:
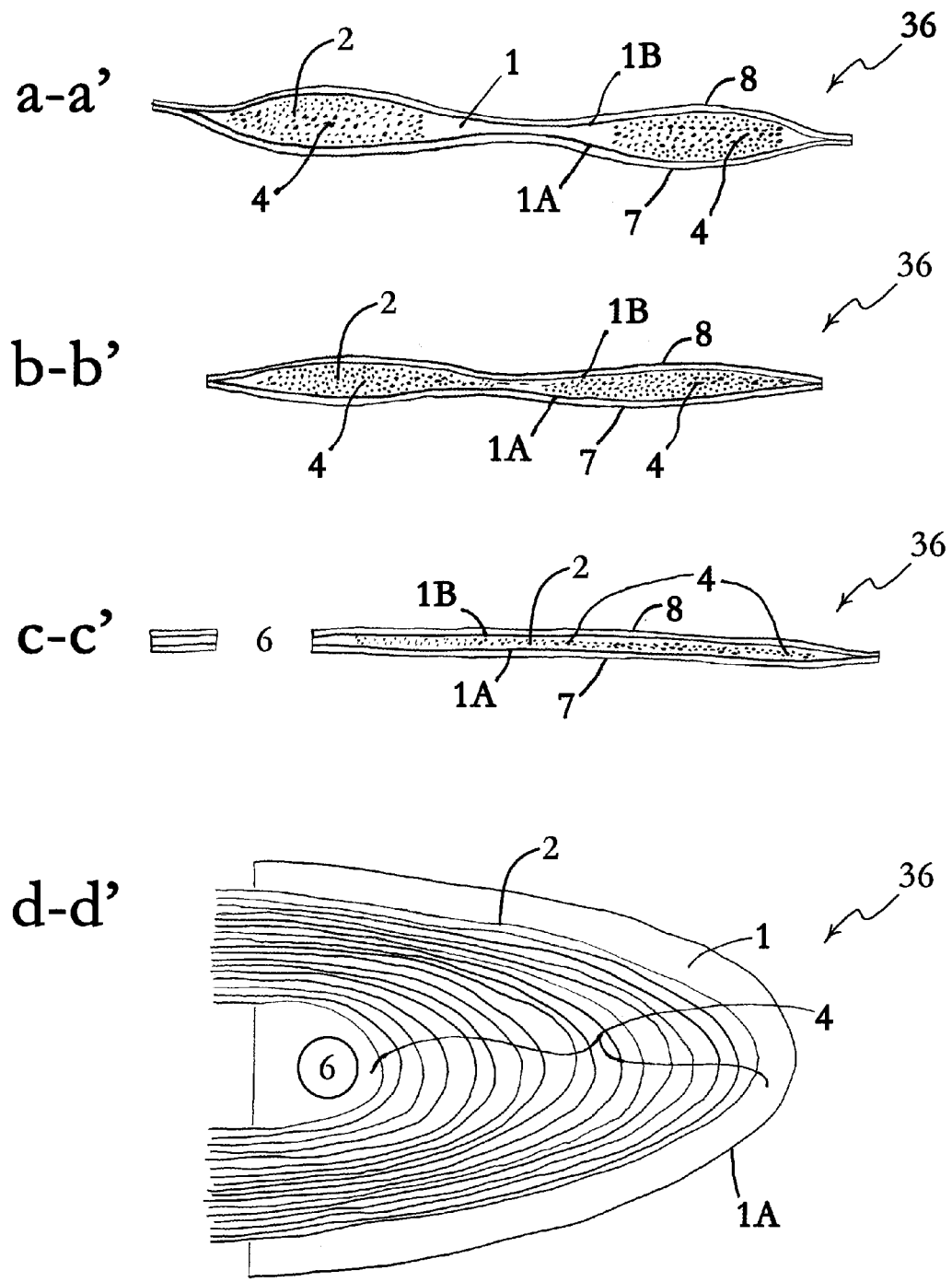
FIG. 2a is a cross-sectional view of the central layer of FIG. 1 with surface membranes taken along line a-a' to provide a prosthetic anchor in accordance with the present invention.
FIG. 2b is a cross-sectional view of the central layer of FIG. 1 with membranes taken along line b-b' to provide a prosthetic anchor in accordance with the present invention.
FIG. 2c is a cross-sectional view of the central layer of FIG. 1 with membranes taken along line c-c' to provide a prosthetic anchor in accordance with the present invention.
FIG. 2d is another view of the central layer of FIG. 1 illustrating approximately half way between the two surface membranes of FIGS. 2a-2c to provide a prosthetic anchor in accordance with the present invention.
Figure 3:
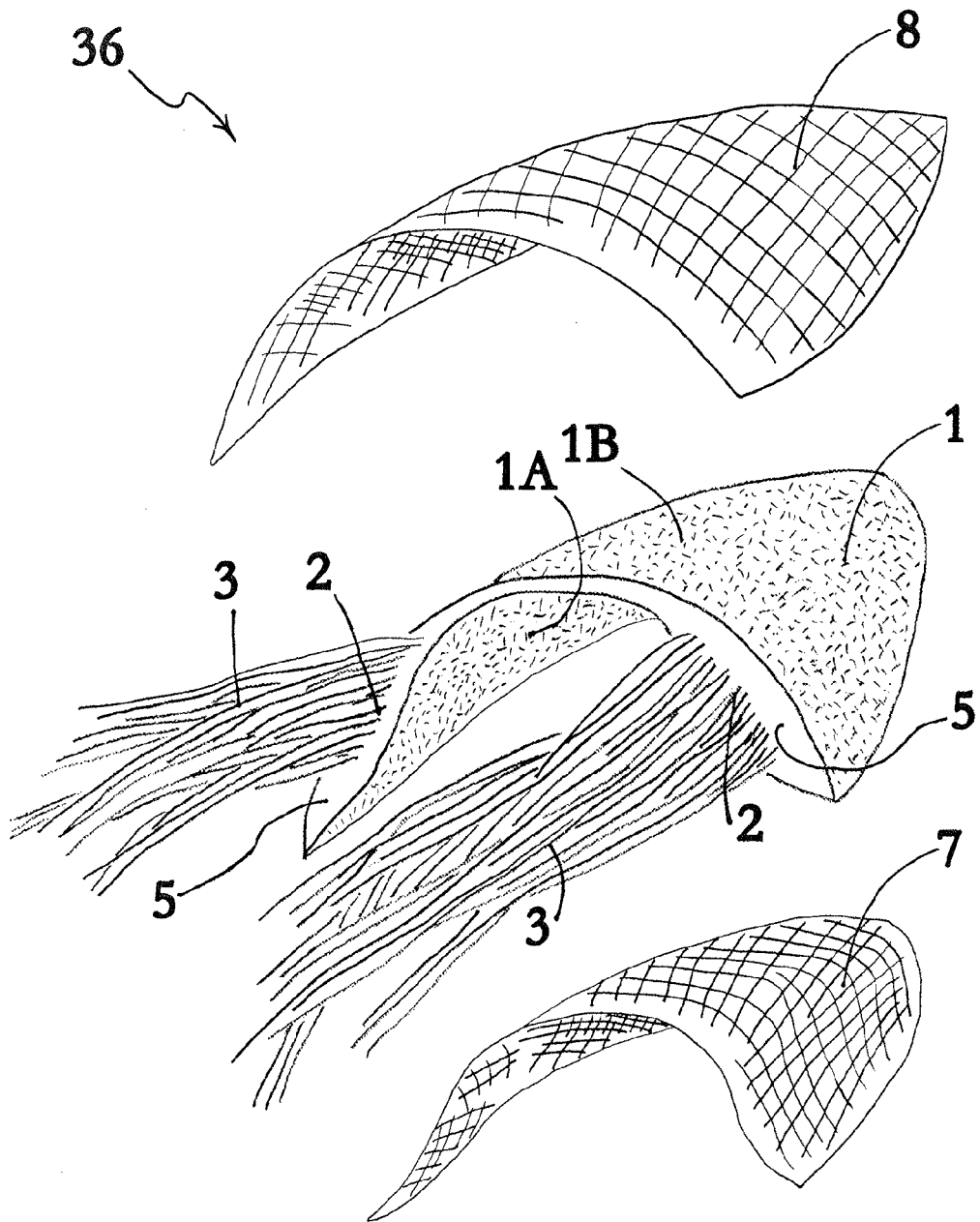
FIG. 3 is an exploded view of a prosthetic anchor in accordance with the present invention including a central layer with thin semi-rigid surface membranes on either side.

As best shown in FIGS. 1-3, the prosthetic anchor (36) generally includes the following three layers:

(a) a central layer (1) of wafer-like structure through which embedded fibers (2), defining a matrix, pass in defined pathways (4). Examples of materials of the central layer (1) include polymers such as elastomeric material, e.g. silicone rubber and polyurethane. The fibers may include natural material (e.g. human and/or animal tendons or ligaments) and/or synthetic materials such as polyester defining a tendon or ligament.

(b) a 'deep' surface membrane (7) which interfaces with a hard structure, such as by being anchored to, for example, a prosthesis, a bone, or other hard tissue. Examples of materials of surface (7) are titanium alloy or other metal, fiber (e.g., carbon, glass)/epoxy composites, and combinations of metals and fiber composites.

(c) a 'superficial' surface membrane (8) which interfaces with adjacent tissue and may be configured to adhere or not to adhere to that tissue. Examples of materials of surface (8) are titanium alloy or other metal, fiber (e.g., carbon, glass)/epoxy composites, and combinations of metals and fiber composites.

The deep and/or the superficial surface membranes (7, 8) may have one or more projections such as posts or needles, as further described below, that extend through openings in the elastomeric central layer (1) to provide counter force to fibers as fibers are tensed. In addition, it should be understood that the surface membranes (7, 8) are optional insofar as the central layer (1) may be adapted to function alone, or with one surface membrane (7 or 8), thereby defining the prosthetic anchor (36).

With further reference to FIGS. 1-3, embedded fibers (2) traverse the central layer (1). Fiber bundles (3) enter and exit the wafer-like layer (1) generally on the same aspect thereof, and within the central layer (1) the embedded fibers (2) traverse concentric substantially parabolic pathways (4). The elastomeric material near edge (5) of the central layer (1), at which fiber bundles (3) enter and exit, may be thicker than in other regions so as to lessen and distribute local stress concentration effected by tension on fiber bundles. Adjacent the concentric fiber pathways (4), there may be an opening (6) which may serve to accommodate either a post or projection (32) (See FIG. 13b) during fabrication, a compression member providing counter-force when tension is applied to the fibers, or both. As best shown in FIGS. 2a-2d and 3, the semi-rigid surface membranes (7, 8) envelop the elastomeric layer (1) and preferably are adherent to it.

Figure 4:
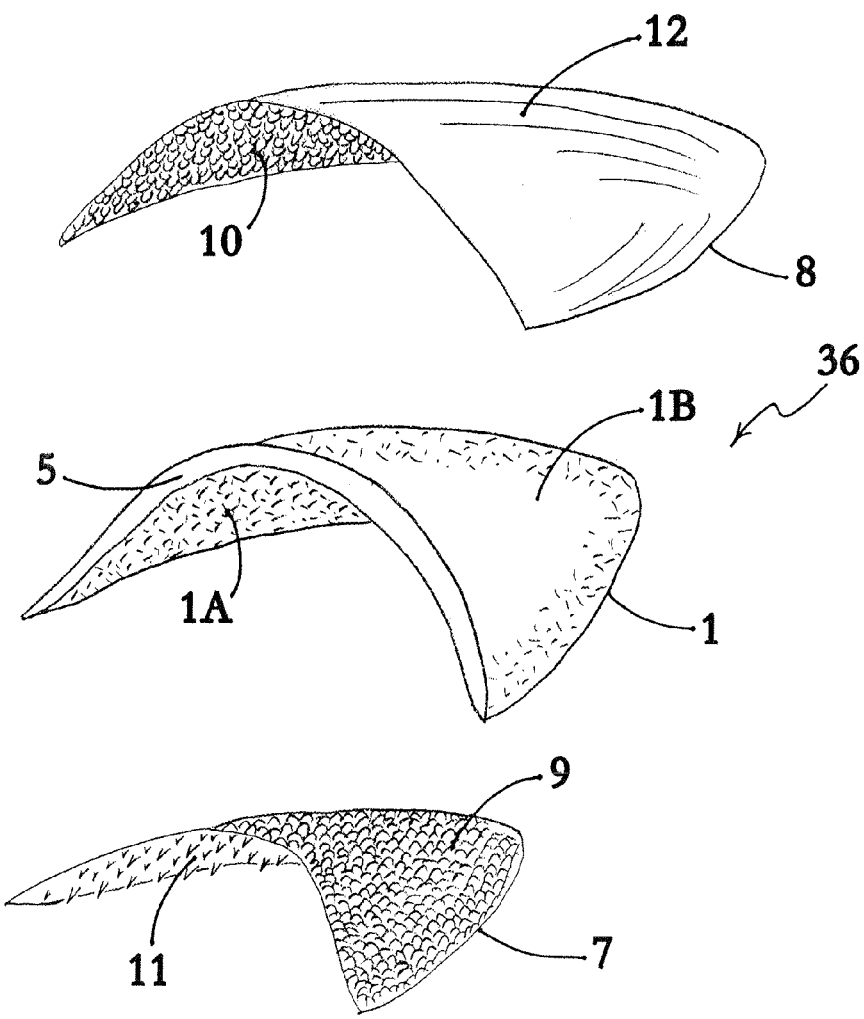
FIG. 4 is an exploded view of another embodiment, similar to that of FIG. 3, with surfaces that are altered wherein the surfaces facing a central layer are textured to adhere to the matrix material, the outer surface of the superficial membrane is polished and smooth (as would be chosen to face skin), and the outer surface of the deep membrane is spiked (as might be chosen to fix to bone)

FIG. 4 shows another embodiment of the device (36) of the present invention (fibers not shown for simplicity) wherein surfaces (9, 10, 11, and 12) are altered. More specifically, those surfaces (9, 10) facing central layer (1) are textured to adhere to the matrix material. The outer surface (11) of the deep surface membrane (7) is spiked, which might be chosen on one non-limiting example of surface alteration to facilitate fixation to bone; other examples are incorporation of textured metal plates, barbs, or meshes in that surface (11). The outer surface (12) of the superficial surface membrane (8) is polished and smooth as may be chosen to face skin and generate a sliding, bursa-like interface.

FIGS. 5 through 23 illustrate non-limiting examples for fabricating the prosthetic anchor (36) in accordance with the present invention.

Figure 5:
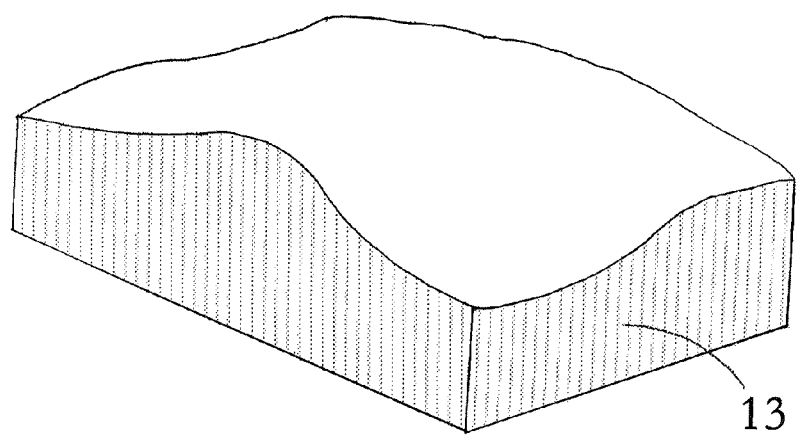
FIGS. 5 through 23 illustrate one or more non-limiting examples for fabricating a prosthetic anchor in accordance with the present invention.

FIG. 5 shows step (a) wherein a block surface (13) of polished steel, polished ceramic, glass-filled epoxy polyester resin or other material, is produced, e.g. machined, molded, or cast as appropriate, in the form of the surface to which the device (36) is to be attached. Alternatively, the actual target anchoring surface may be used such as the mechanical interfacing part of a cardiac prosthesis, or an excised anatomically typical bone with appropriate lacquering, or other surface treatment.

Figure 6:
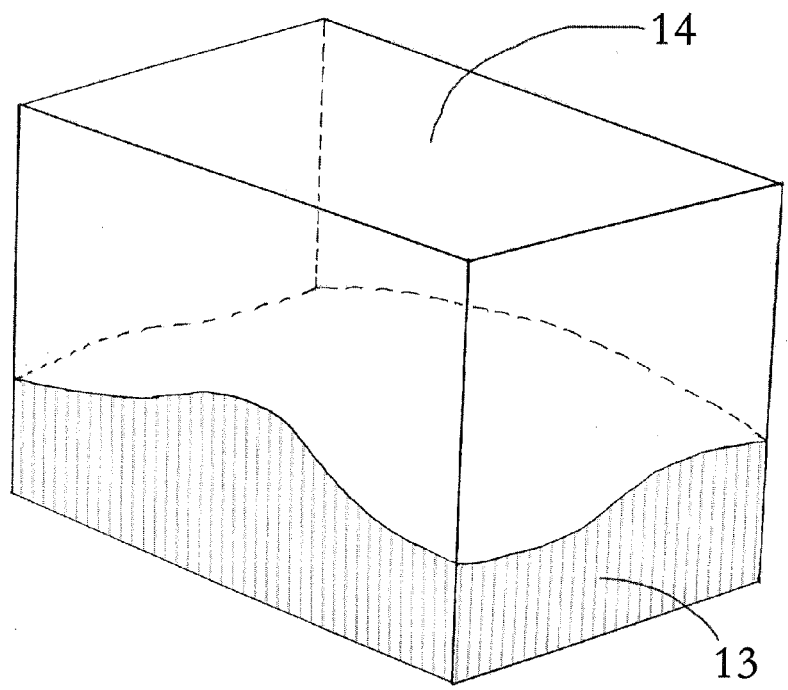
Figure 7:
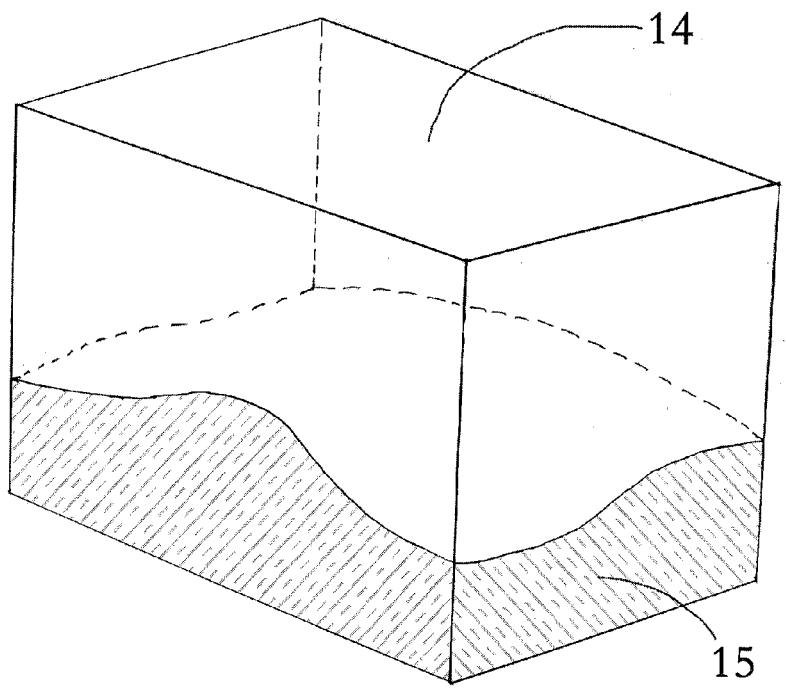

FIG. 6 shows step (b) wherein the surface, or surface replica (13), is used to form a mold (14) of a soft elastomeric material such as a polyurethane or silicone rubber. Mold or part (14) is termed "fabrication part A" in the continuing description. FIG. 7 shows step (c) wherein a hard mating surface (15), such as a glass-filled epoxy polyester resin or other material, is cast. This mating surface (15) is a replica of the applicable surface of part 13. Hard mating surface (15) is termed "fabrication part B" in the continuing description.

Figure 8:
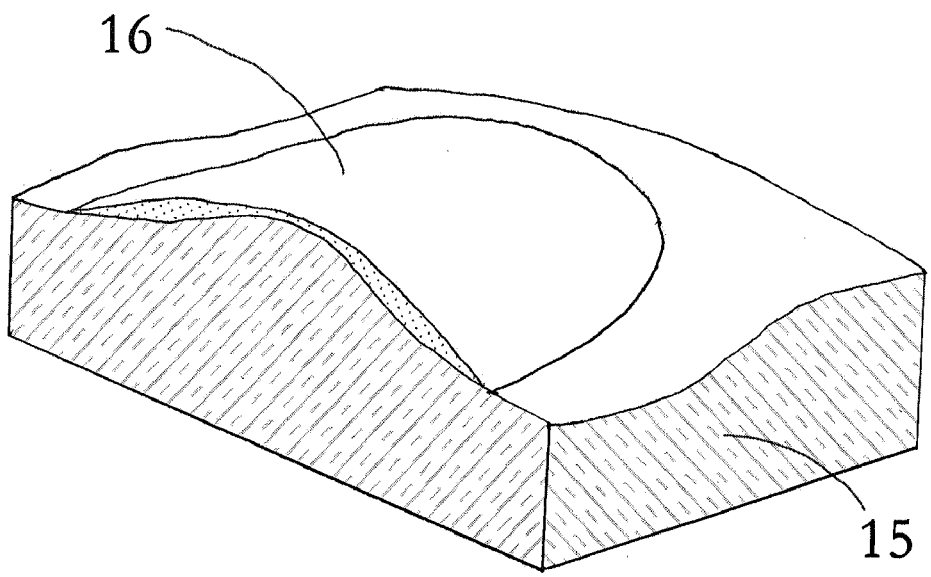
Figure 9:
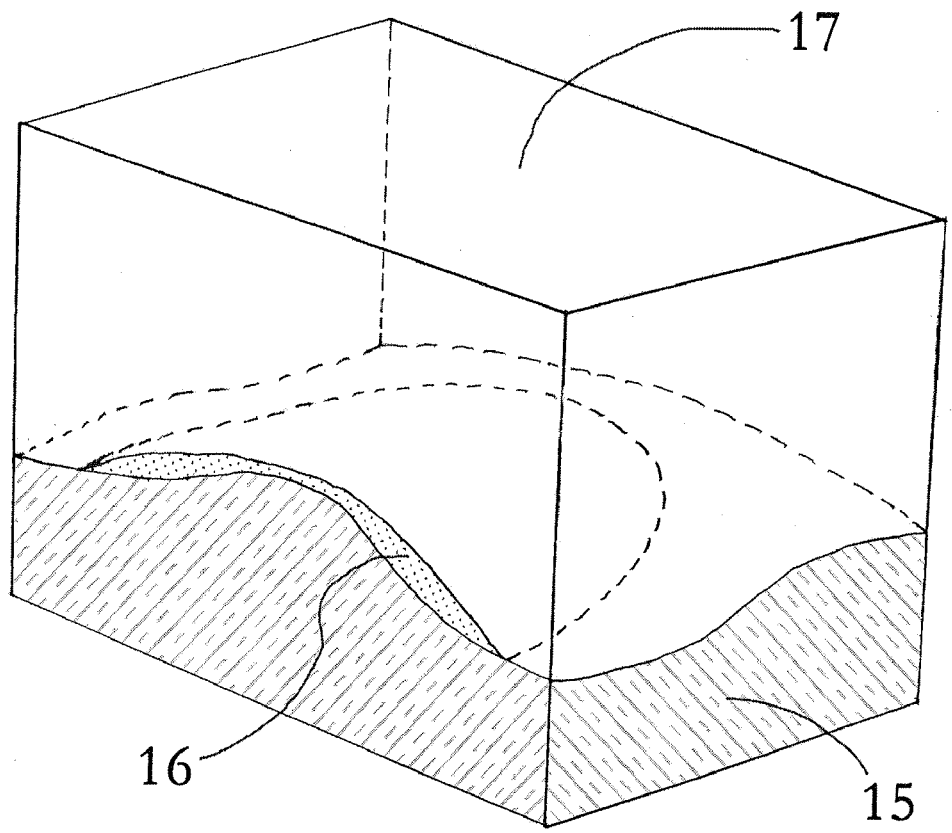

FIG. 8 shows step (d) wherein a clay wafer (16), or a wafer of curable clay-like modeling polymer, whose geometry mimics the desired geometry of the anchor (36) is formed on the surface of fabrication part B (15). The wafer (16) is cured or hardened to produce "fabrication part C." FIG. 9 shows step (e) wherein, after applying liberal mold-release agent(s), a hard outer cast (17) is formed to mate with the fabrication parts B (15) and C (16) assembly. The outer cast (17) is termed "Fabrication part D" in which two parts, i.e. an inner and outer section, are made.

Figure 10:
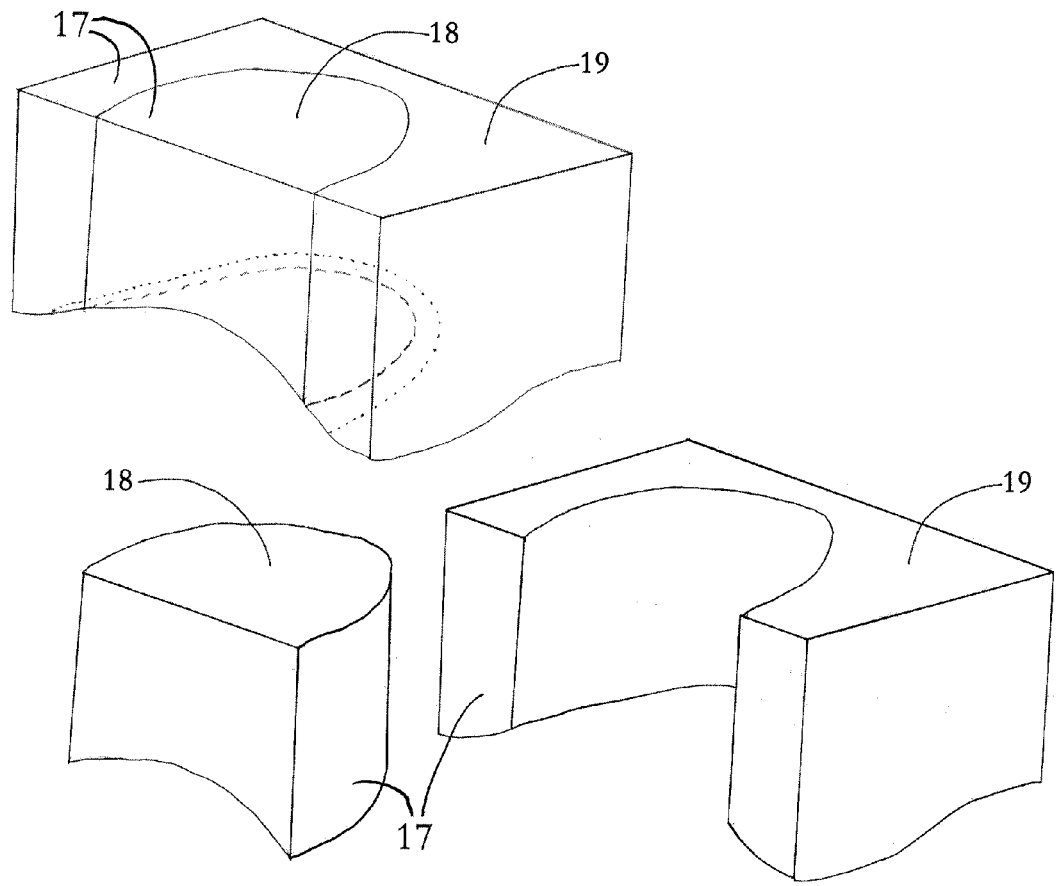
Figure 11:
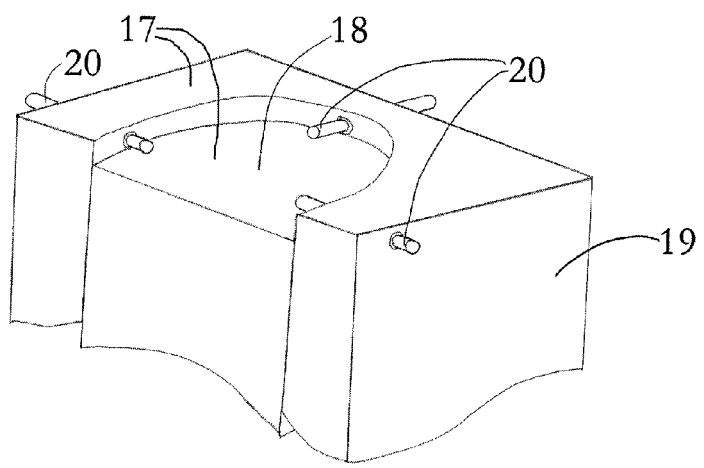

FIG. 10 shows step (f) that includes using a scroll saw, a wire cutter, a laser beam, or other tool, so that Fabrication part D (17) is cut a short distance, generally 2-3 mm inside, and concentric to the margin of Fabrication part C (16) to form an inner section (18), "fabrication part E" and an outer section (19), "fabrication part F." FIG. 11 shows step (g) wherein Fabrication part F (19) is positioned offset from its original position on Fabrication part E (18) by a short distance, approximately the thickness of a diameter of a fiber tow (28), to facilitate step (m) (See FIG. 17) described below, generally 1 to 3 mm, and held in place by a removable pin (20) or other means.

FIGS. 12a-12g illustrate step (h) wherein a multilayer fiber/polymer composite layup with carbon-fiber/epoxy and glass fiber/epoxy, either manually saturating or utilizing pre-impregnated sheets, is formed between the mating surfaces of Fabrication parts A and B (14, 15), and cured under compression to form the deep semi-rigid surface membrane (7). Part or all of either surface of the deep or superficial surface membranes (7, 8) may be a smooth surface (21). One or more strips or plates of textured or sintered metal plates (not shown), metal mesh (22) or other materials designed for adhering to the bony or other mounting surface may be incorporated between the composite layup and Fabrication part A (14), underlying all or part of that surface. The degree of metallic or other material underlayment is dependent on design goals, particularly desired regional flexibility or rigidity.

Figures 12A, 12B, 12C, 12D, 12E, 12F, 12G:
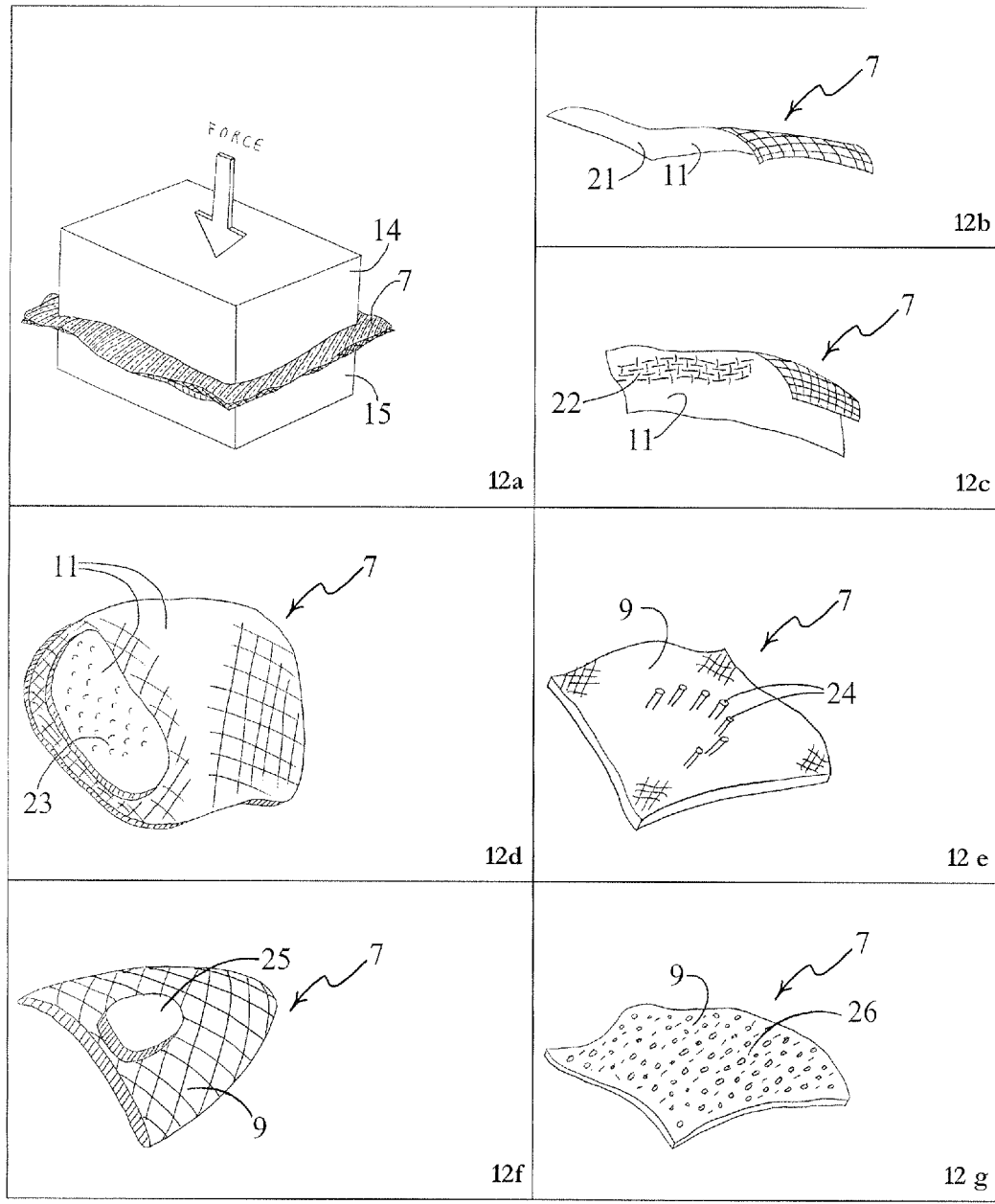

Specifically, FIG. 12*a* shows the process of forming the composite layer under pressure, while FIGS. 12*b*, 12*c*, and 12*d* show a non-limiting set of possible variations in the outer or deep surface of the deep layer surface membrane (7): smooth (21) in FIG. 12*b*, incorporating metal mesh (22) in FIG. 12*c*, and/or textured metal plate (23) in FIG. 12*d*. FIGS. 12*e*, 12*f* and 12*g* show further variations in the superficial surface of the deep layer (7). FIG. 12*e* shows a composite layer with short needle-like projections (24) in the superficial surface of the deep surface membrane (7), formed either by drilling appropriate holes in the mating surface of Fabrication Part B (15) or by adding metallic or other projections or 'tacks' to Fabrication Part A (14) prior to the layup. These are shown in an array chosen to support the fiber placement procedure described below in FIG. 17, step (m). FIG. 12*f* illustrates a deep composite surface membrane (7) with a peg-like central plateau (25) that serves the same purposes of the needle-like projections (24) of FIG. 12*e*. Finally, FIG. 12*g* shows a roughened, textured (26) portion of superficial surface of the deep composite membrane such as may be effected, for example, by preliminary mechanical pitting of Fabrication part B (15). Features 22 through 26 may be used in any combination or used alone.

Figure 13A:
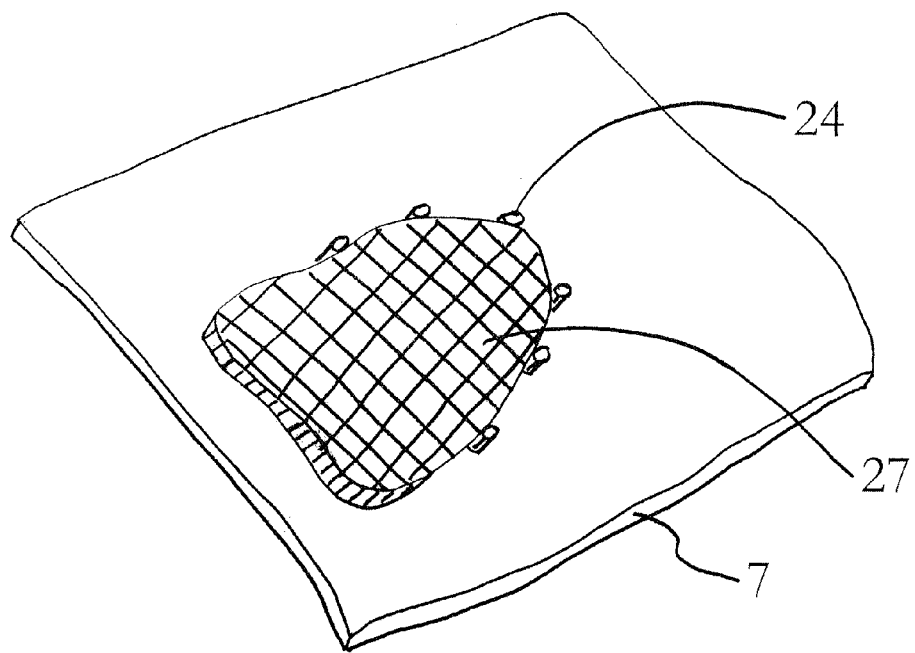
Figure 13B:
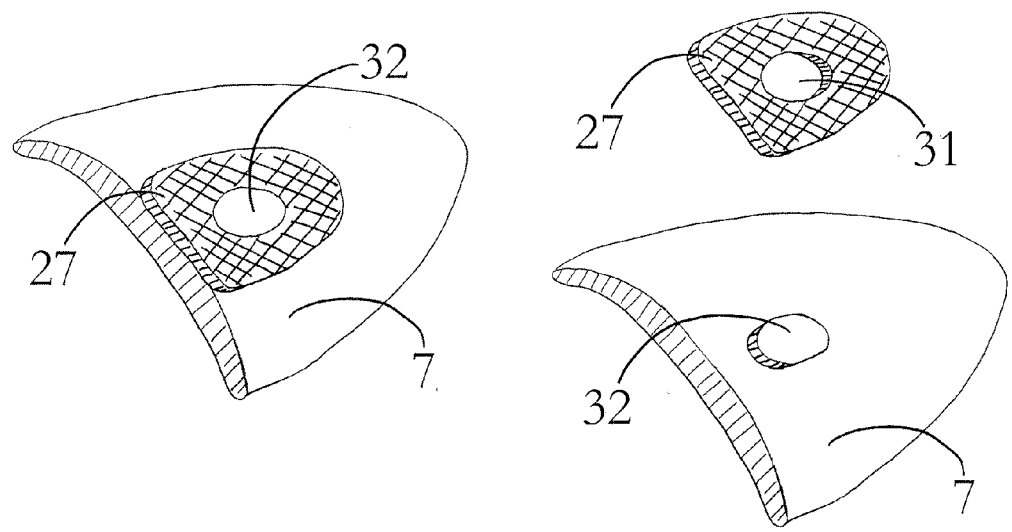

FIG. 13*a* shows step (i) wherein a generally parabolic disc (27) of porous biocompatible material, such as a polyester fabric, in one or more layers is saturated in uncured silicone rubber or other elastomeric resin and positioned on deep surface membrane (7) aligned with projections (24) of the type illustrated in FIG. 12*e*. Alternately, as shown in FIG. 13*b*, a hole (31) in the fabric or other disc material (27) can be configured to fit about one or more broader peg-like plateaus or projections (32) from the superficial surface of the deep surface membrane (7). The fabric disc (27) is separated from the deep surface membrane (7) in the right of the two drawings for clarity, and in actual position on the left.

Figure 13C:
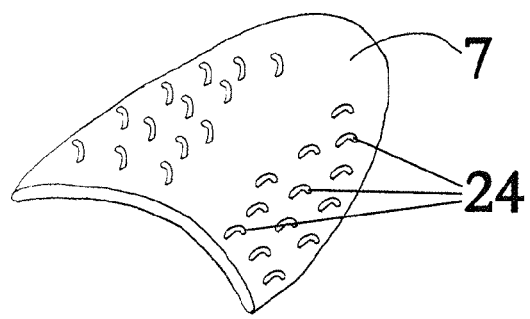

FIG. 13*c* shows a series of projections (24), which may or may not be hook-like in configuration, extending superficially from the deep surface membrane (7) to stabilize and support various concentric groups of fibers during casting of the fiber/elastomeric-matrix composite wafer (1). These will be generally positioned in two or more concentric curved rows of two or more projections. For example, FIG. 13*c* shows three concentric rows having six, eight, and twelve projections (24), respectively.

Figure 14:
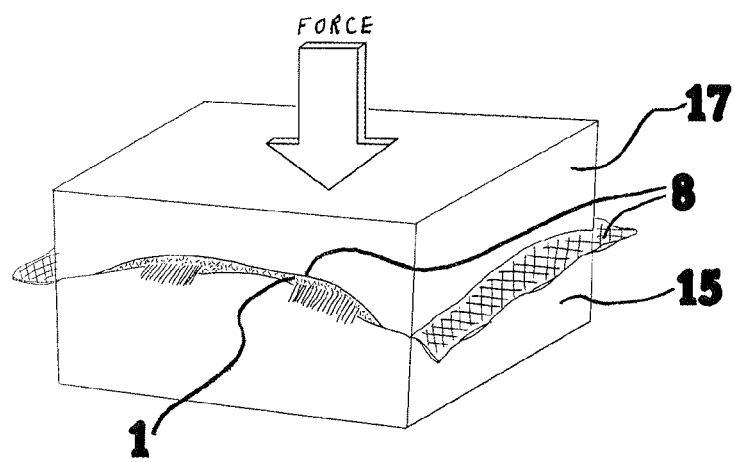
Figure 15:
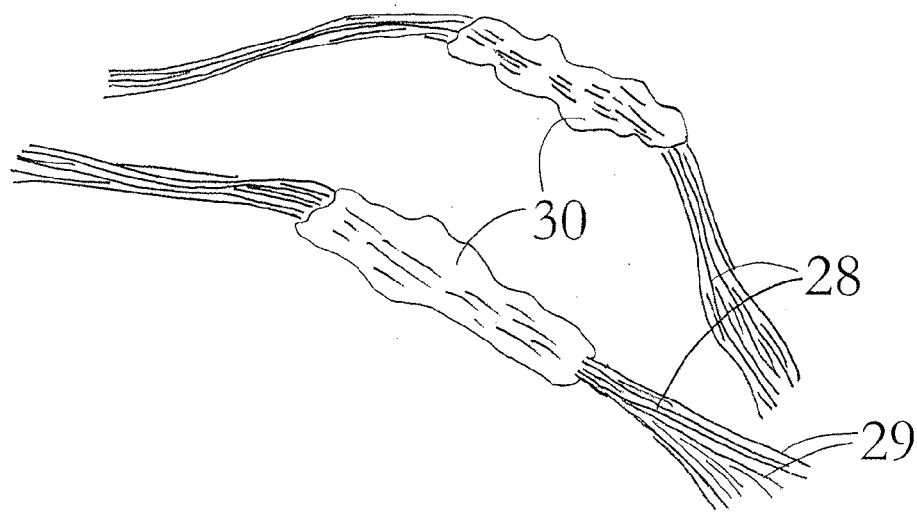

FIG. 14 shows step (j) wherein the uncut Fabrication Part D (17) and Fabrication Part B (15) are held together in compression on opposite sides of the central layer (1) and cured to form the superficial surface membrane (8). FIG. 15 shows step (k) wherein bundles or tows (28) of individual coupler fibers (29), generally of a polymer such as polyester, generally 6 to 20 microns in diameter, and generally in tows or bundles (28) of several dozen to several thousand each, are saturated with uncured elastomer resin in their central regions (30).

The next steps describe three general embodiments of non-limiting example of methods for stabilizing fibers and embedding them within the elastomer of the central wafer-like layer (1).

Accordingly, FIGS. 16-20 (steps l through p), as further described below, illustrate a method of stabilizing fibers, pending elastomeric matrix curing, by opposed rigid restraining surfaces and, more specifically, illustrate one method of insinuating bundles (28) between two restraining surfaces and sequentially tensing each bundle against the bundle concentrically inside it wherein the separation distance of the two restraining surfaces determines how thick or thin (i.e., how concentrated or spread out) the fibers are at a particular location. In this method, the innermost fiber bundle is supported by a generally parabolic disc of porous material, one or more projections (peg or needle-like) from one of the surfaces, or both.

Figure 16:
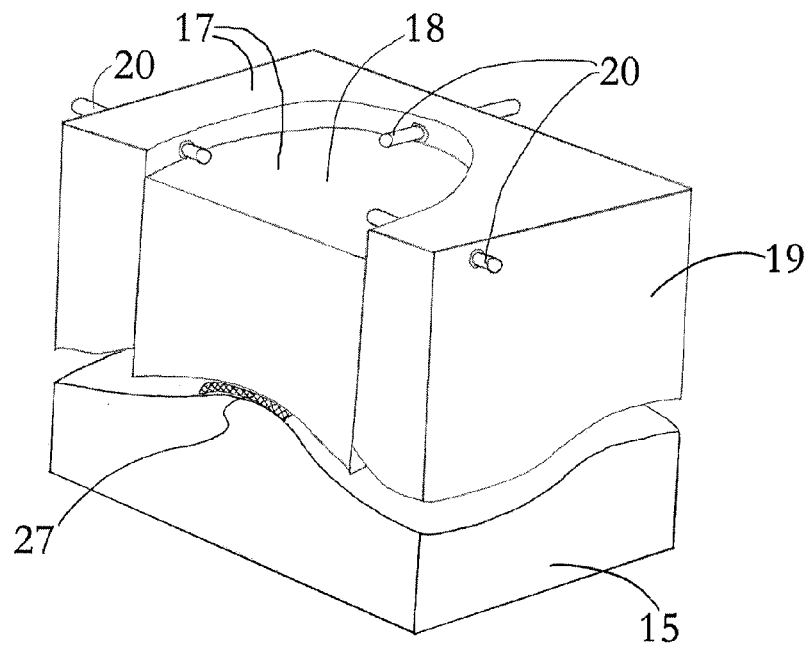
Figure 17:
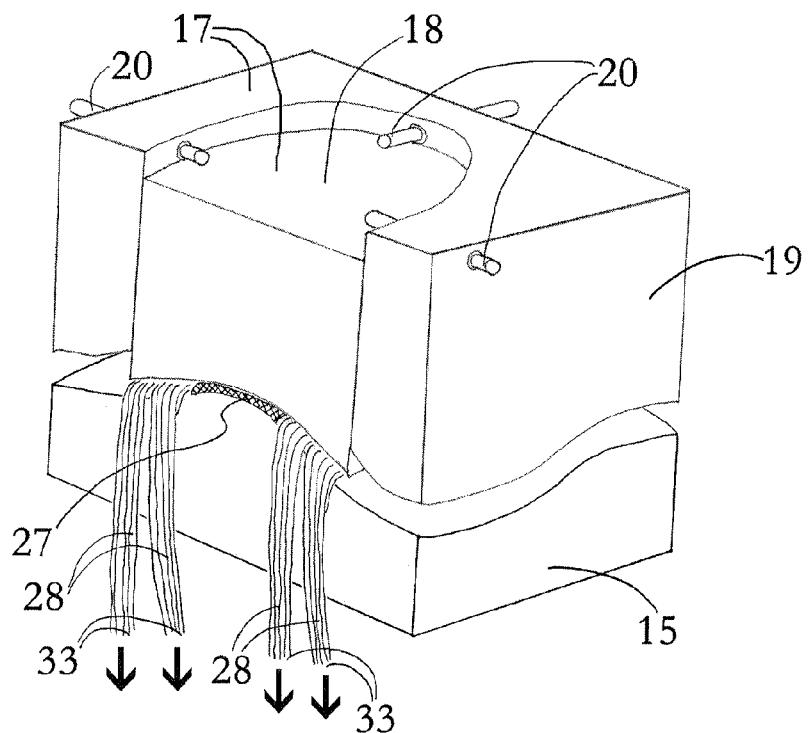

FIG. 16 shows step (l) for fabricating device (36). More particularly, assembled fabrication parts E (18) and F (19) (as in step g) are placed on the surface of the fabric disc (27) and clamped rigidly so that a space is left approximately the thickness of a diameter of a fiber tow (28) between parts F (19) and B (15). FIG. 17 shows step (m) wherein each of the one or more tows or bundles (28) of fibers, with tension on either end (33), are insinuated between the margins of fabrication parts F (19) and B (15). The tows or bundles (28) of fibers are maneuvered centrally by maintenance of that tension until each lies between fabrication parts E (18) and B (15), and are sequentially held securely against, first, the fabric disc (27), and then against prior bundles, progressing concentrically outward.

Figure 18:
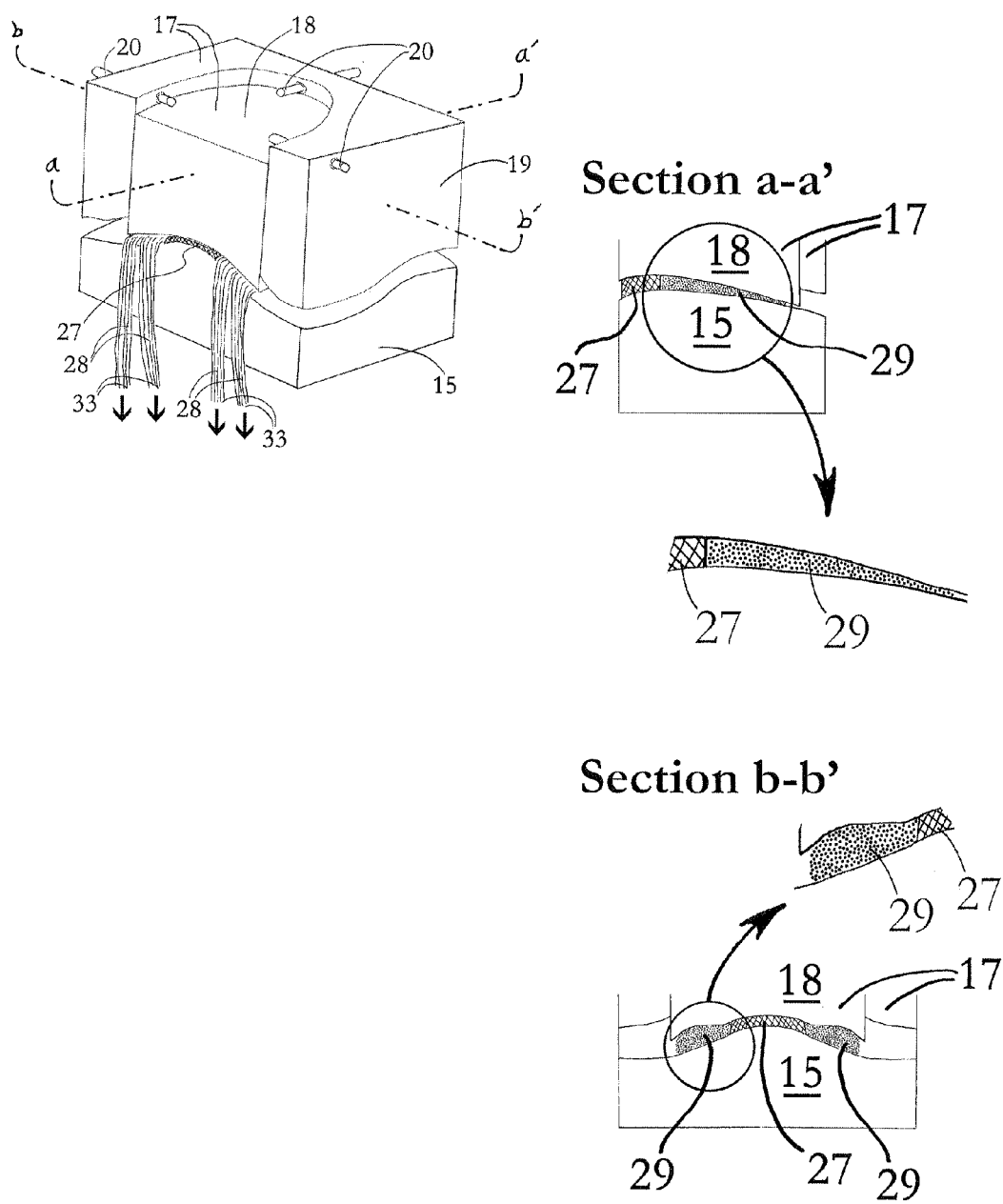

FIG. 18 shows step (n) wherein the varying thickness of the space between fabrication parts E (18) and B (15), as determined by the varying thickness of Fabrication part C (the clay wafer 16—See FIG. 9) used to mold part E (18), determines in turn the varying thickness of the fiber layer as it progresses radially away from the central disc (27). The fiber layer may progress differently in terms of distance covered per number of fibers (29), at different points around the central disc (27), dependent on this varying thickness profile. For the non-limiting example shown, the center of the irregular approximately 180° wrap is thinner and wider than are the sides.

Figure 19:
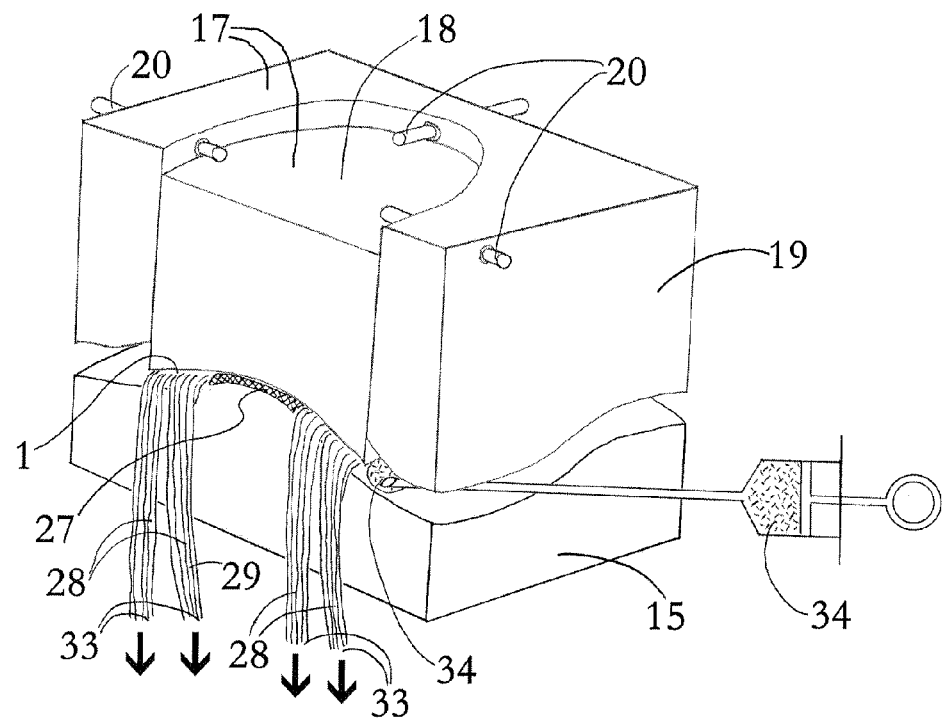
Figure 20:
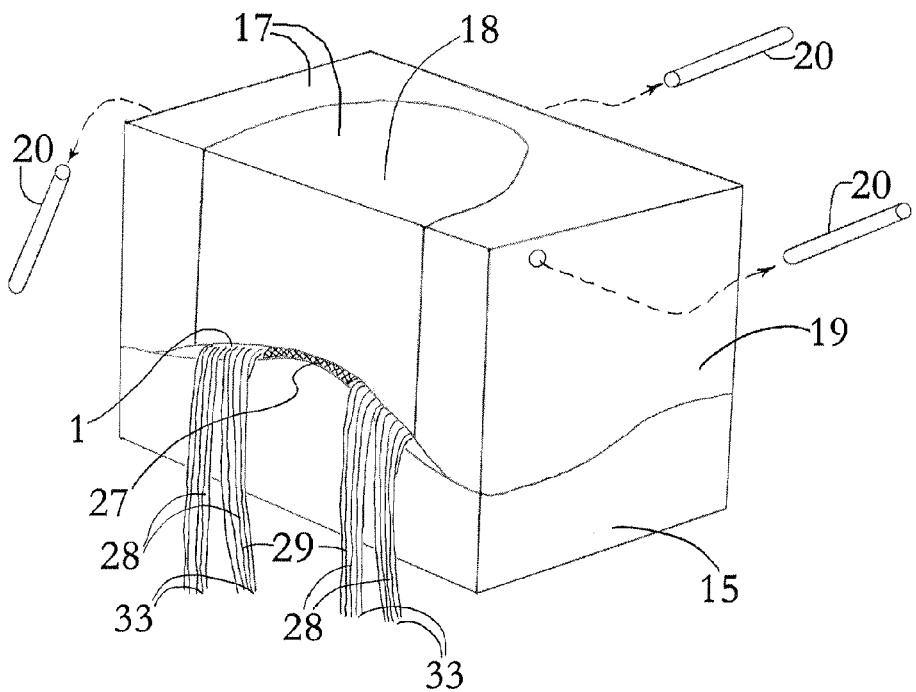

FIG. 19 shows step (o). When the desired number of fibers (29) have been placed, and either end (33) of each bundle (28) of fibers secured by tension, either of weight or elastic or other mechanism, a strip of uncured elastomer (34) is applied peripherally to form the central layer (1). FIG. 20 shows step (p) wherein the temporarily securing pins (20) are removed to allow Fabrication Part F (19) to be advanced on Fabrication Part E (18) until it contacts Fabrication Part B (15), expressing excessive uncured elastomer, and compressed against Part B (15) while the elastomer is cured to form the central layer (1).

Figure 21:
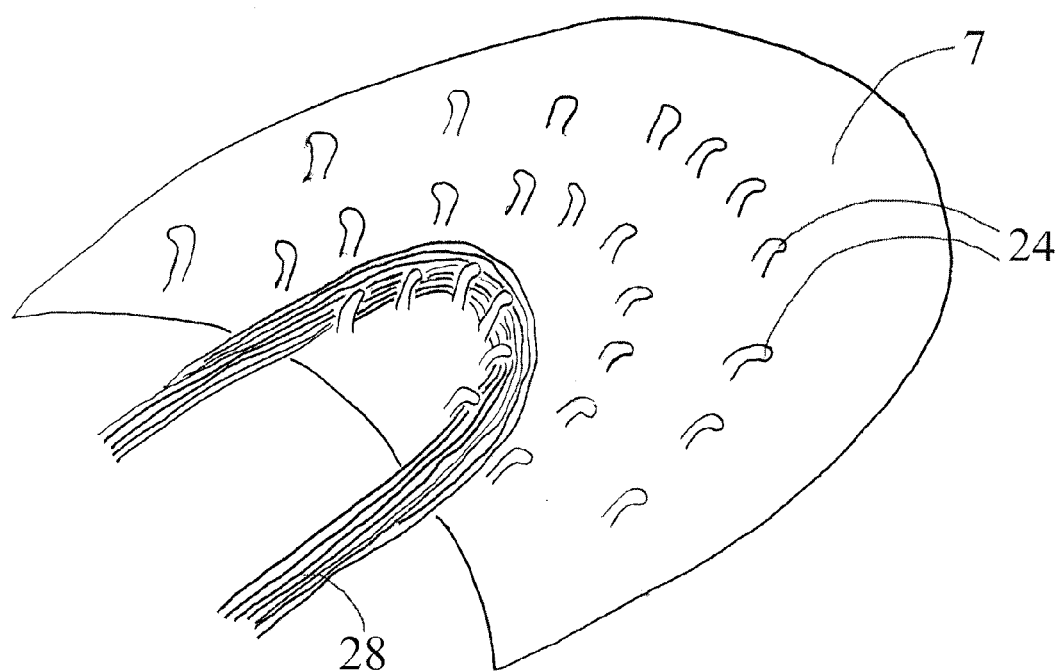
Figure 22:
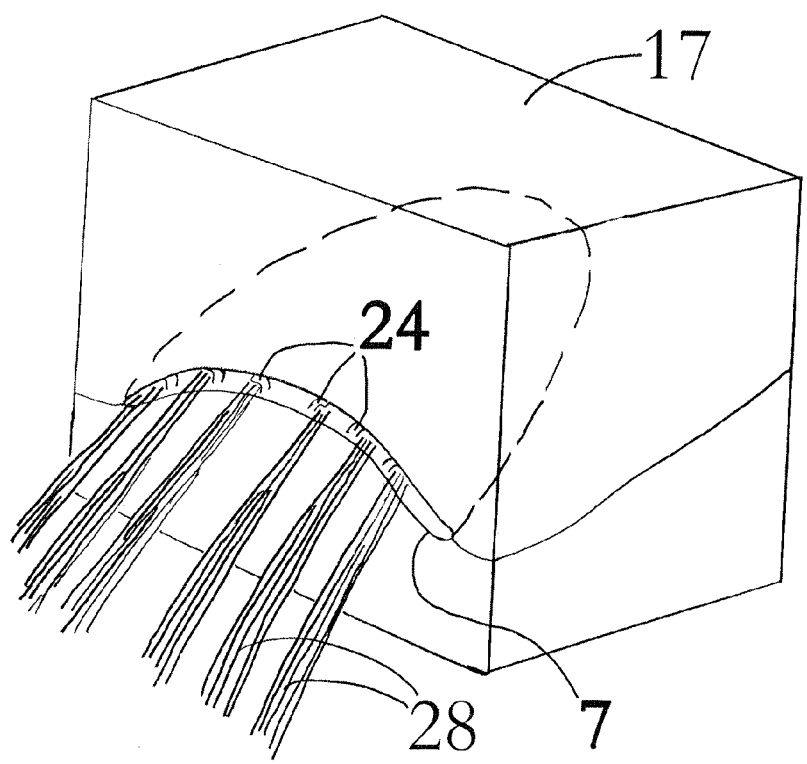

FIGS. 21 and 22 (steps q and r) show another nonlimiting example of a method of stabilizing fibers, pending elastomeric matrix curing, by needle-like projections (24) from one or both of the enveloping membranes (7, 8) and, more particularly, illustrate one method in which there are two or more concentric curved rows of needle-like projections (24), which may be hook-shaped, from one of the enveloping membranes (7) wherein the membrane may be of any of a range of metallic, fiber-matrix composite, or other materials.

Figure 23:
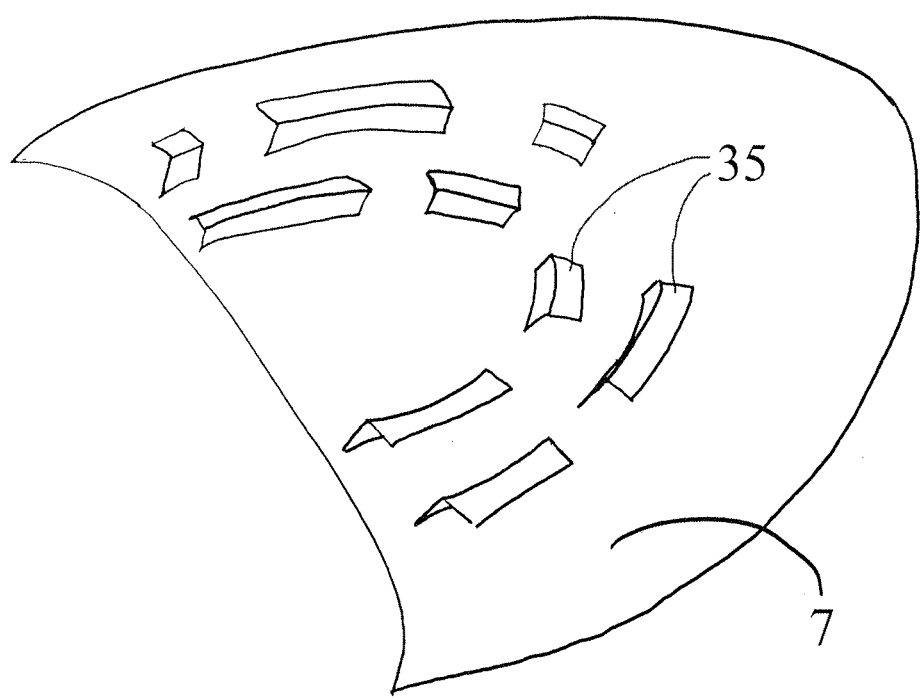

Specifically, in step (q), FIG. 21 illustrates each elastomer-saturated bundle, or group of one or more bundles (28), placed around one concentric row of hook-like extensions (24), one at a time, progressing outwardly, and placed under tension until all bundles are in place. Accordingly, it should be understood that the extensions (24) may be provided on one or both of the surface membranes (7, 8). Next, in step (r), FIG. 22 illustrates the uncut part (17) or "Fabrication part D" that is positioned on the surface of projections (24) and bundles (28), pressure is applied, and the central layer (1) cured similar to step (p) of FIG. 20. FIG. 23 shows step (s), another variation of step (q) in which, rather than curved rows of hook-like projections extending from membrane (7) or membrane (8), one or more flanges (35) can support successive concentric bundles of fibers.

Dependent upon which method of making as above described has been employed, the appropriate surface membrane(s) (7, 8), such as a carbon-fiber composite or glass-fiber composite, may be applied, e.g. adhesively, to the elastomeric central layer (1) following curing, such as in multiple laminae, to the opposite surface(s) of the central layer (1) to form prosthetic anchor (36). It should be understood that the surface membranes (7, 8) may be optional insofar as the central layer (1) may be provided alone, i.e. without the surface membranes (7, 8), or with only one surface membrane (7 or 8), thereby defining the prosthetic anchor (36). Accordingly, it should be understood that the material of the central layer (1) may be modified to provide the desired flexibility or rigidity and can optionally, or in addition to a suitable polymer, include a carbon-fiber composite or glass-fiber composite with a matrix such as epoxy.

Figure 24:
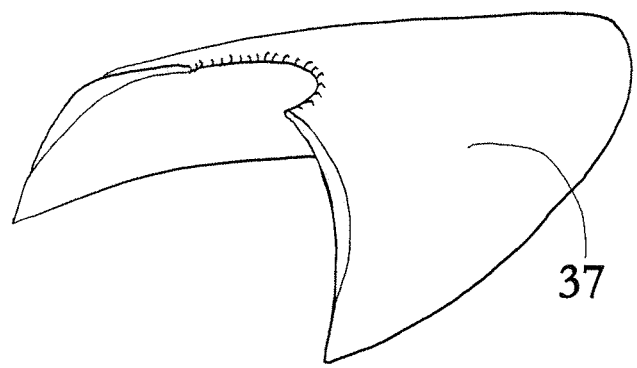
FIG. 24 is a perspective view of a machined or molded bloc replica, or master, of a central layer illustrating another method of fabrication.
Figure 25:
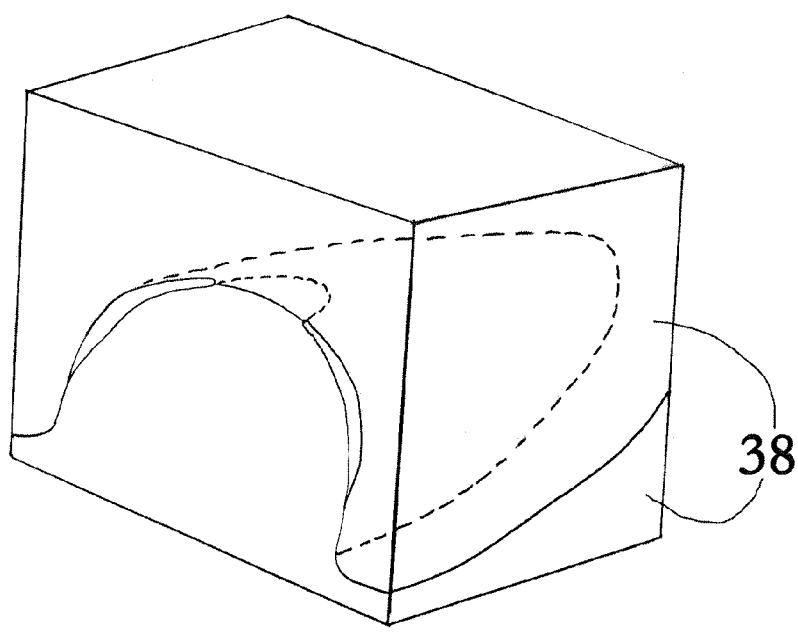
FIG. 25 is a perspective view of a silicone mold of the master of the central layer from FIG. 24.

FIGS. 24 and 25 show yet another alternative method in which an envelope (42) of fiber-matrix composite, such as carbon-fiber/epoxy, can be preformed and fibers inserted with uncured elastomer through one open margin, as further described below, following which the assembly defining the prosthetic anchor (36) is fixed to bone or prosthesis with screws or other means, which also fix the margins of the envelope to each other.

Figure 26:
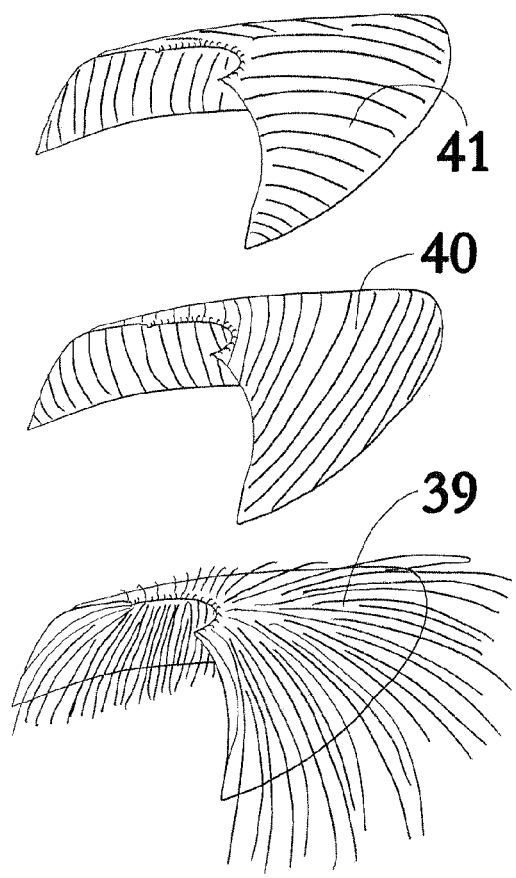
FIG. 26 is an exploded view of radial fibers (carbon, glass, or other), with two diagonal layers in space illustrating an alternate method of fabrication.

More specifically, FIG. 24 shows step (aa) wherein a machined or molded bloc replica, or master (37), of envelope or wafer (42) is provided. FIG. 25 shows step (bb) including providing a two-part silicone mold (38) of the master (37). FIG. 26 illustrates optional step (cc) wherein similar layers or surface membranes could be 'laid up' (not shown) on the deep side of the master (37) as well. In particular, FIG. 26 shows radial fibers (39), such as carbon, glass, or other, with two diagonal layers (40, 41) in space.

Figure 27:
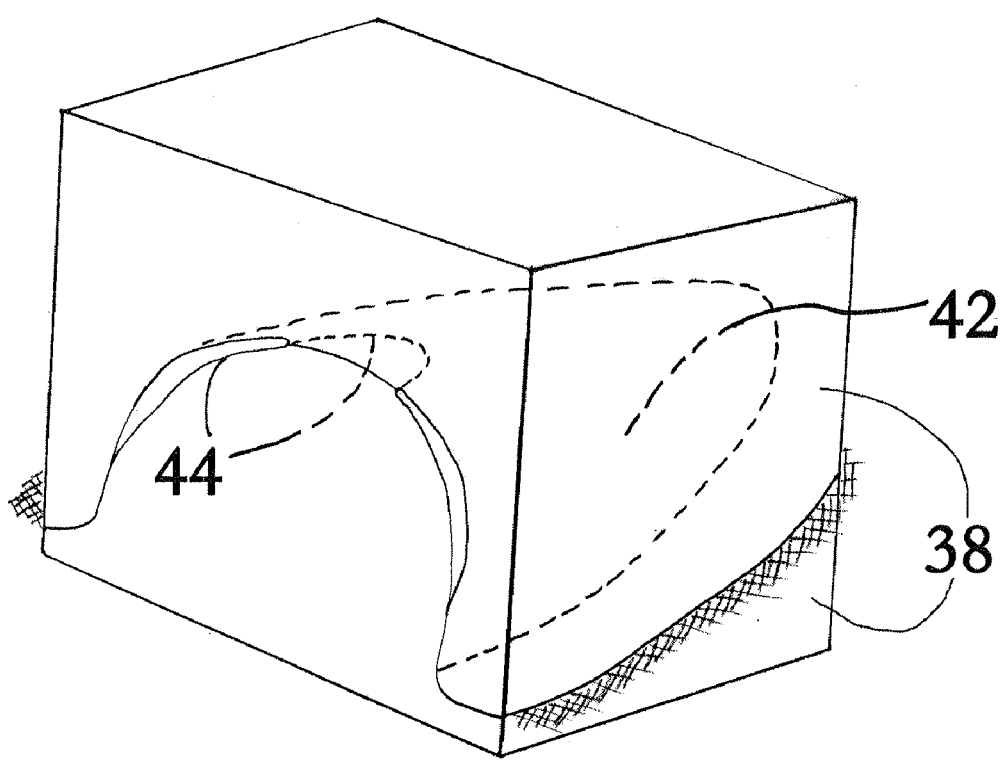
FIG. 27 illustrates curing of a portion of the anchor, in accordance with the present invention, in the mold of FIG. 25.
Figure 28:
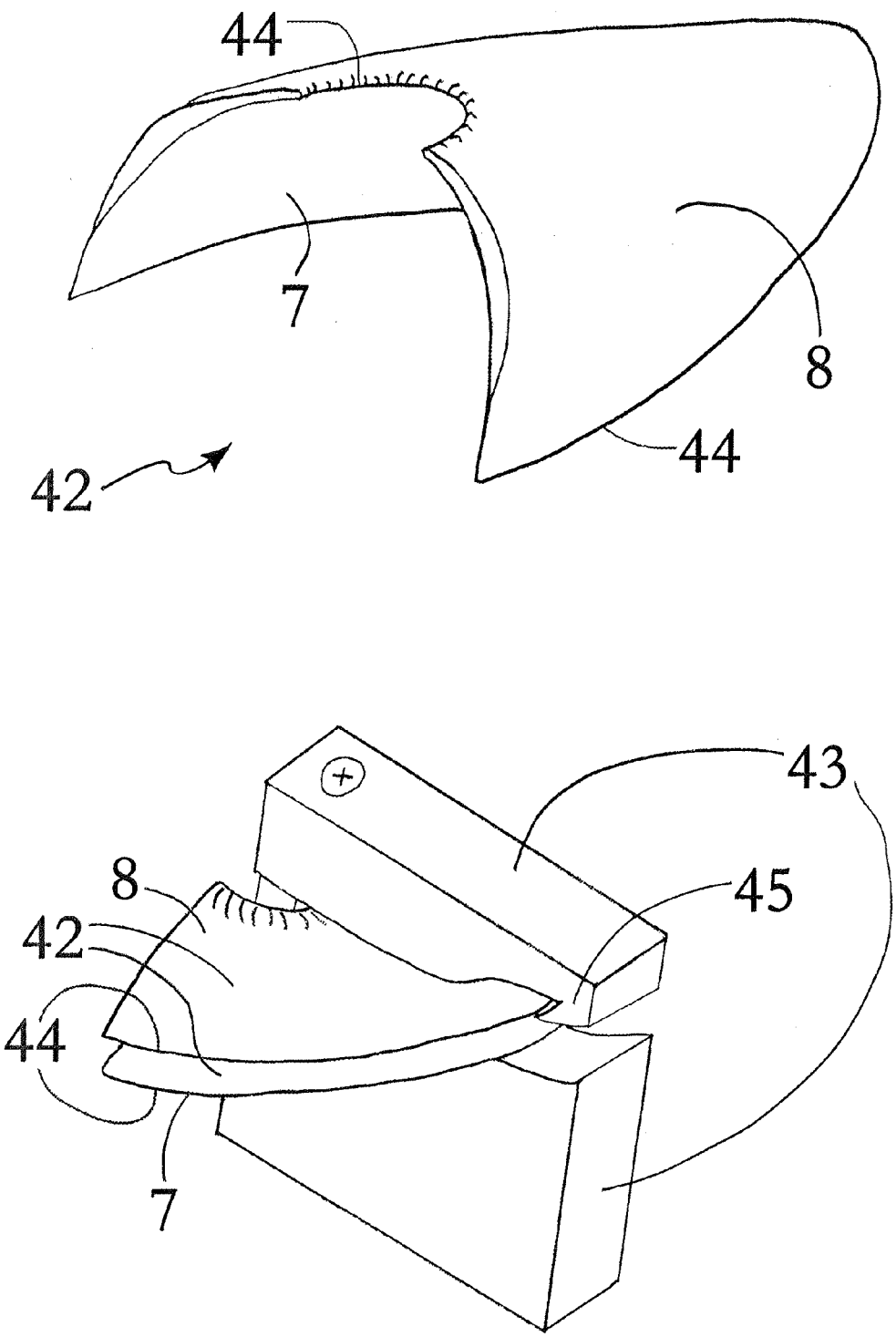
FIG. 28 illustrates a demolded, trimmed, fiber-composite envelope alone (above) and held in clasp (below) for insertion of fibers.
Figure 29:
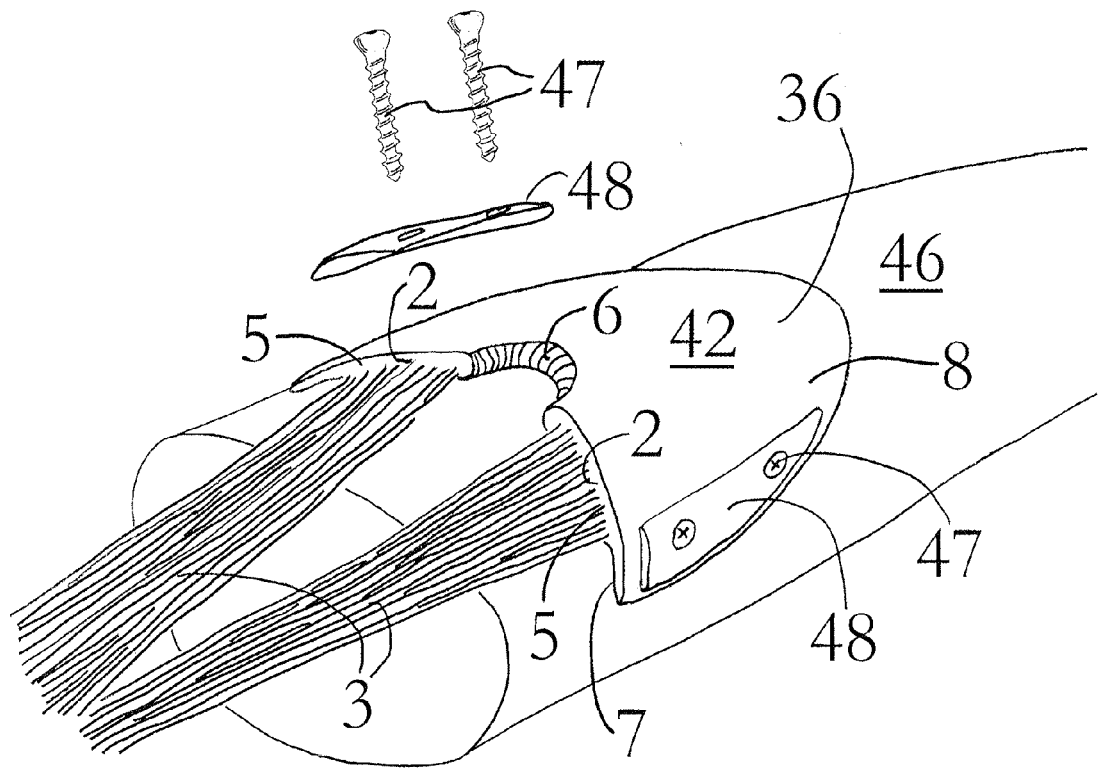
FIG. 29 shows a prosthetic anchor in accordance with the present invention being affixed to bone with screws and metal stress-distributing plates.

FIG. 27 illustrates step (dd) showing curing in mold (38) to form fiber-composite envelope (42). FIG. 28 illustrates step (ee) showing a demolded, trimmed, fiber-composite envelope (42) (above) and held in clasp (43) (below) for insertion of fibers. The outer and inner membranes of the envelope are united only at the margin (44) of the parabolic shaped opening. The clasp (43) has a flange (45) to hold the envelope (42) apart during insertion of fiber tows. FIG. 29 illustrates step (ff) wherein the envelope (42) with inserted fiber tows defining prosthetic anchor (36) is fixed to bone (46) with screws (47) and metal stress-distributing plates (48).

Figure 30:
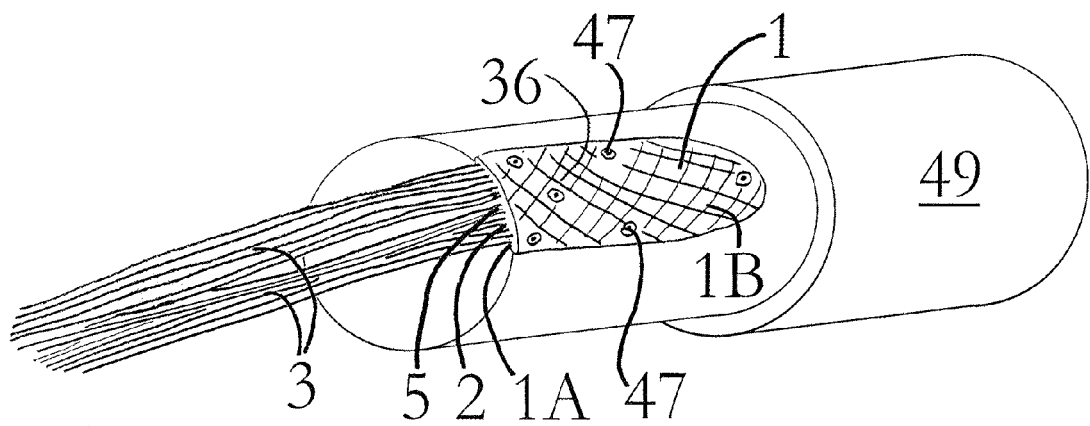
FIG. 30 shows a prosthetic anchor in accordance with the present invention affixed to a hydraulic or other mechanical energy converter.
Figure 31:
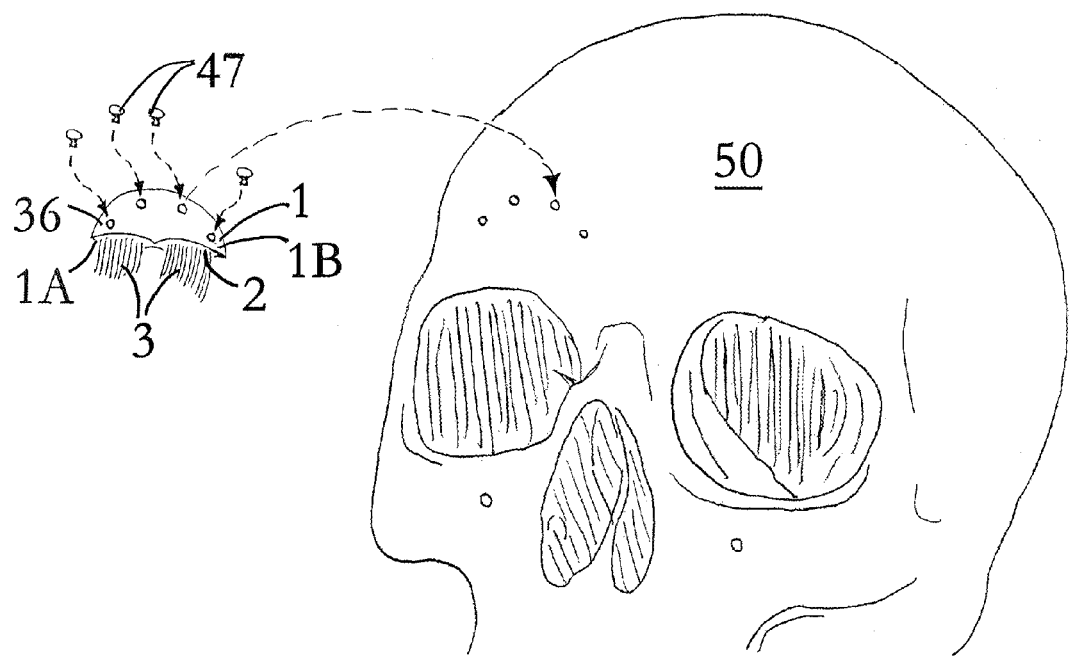
FIG. 31 shows a prosthetic anchor in accordance with the present invention being affixed to a frontal bone.
Figure 32:
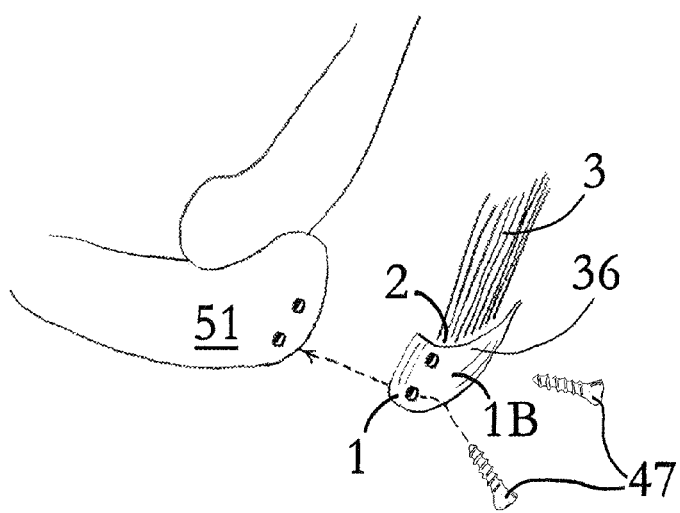
FIG. 32 shows a prosthetic anchor in accordance with the present invention being affixed to an olecranon of an ulna.

FIG. 30 shows an embodiment of the prosthetic anchor (36) as might be applied to terminate and affix to a hydraulic or other mechanical energy converter (49). FIG. 31 shows another embodiment of the invention as might be applied to terminate and fix the prosthetic anchor (36) to a frontal bone (50), as might be desired in the cosmetic surgical procedure of brow lift. FIG. 32 is yet another embodiment of the invention as might be applied to terminate and fix the prosthetic anchor (36) to an olecranon (51) of an ulna, as reconstruction of a damaged triceps tendon.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A prosthetic anchor adapted for attachment to a natural or prosthetic structure of a human or animal, comprising:
    a central layer including a wafer-like structure and a plurality of embedded fiber bundles, each of the plurality of embedded fiber bundles having a medial portion, the medial portions being situated concentrically with respect to one another within the wafer-like structure to substantially define a generally horseshoe-shaped pattern that shares a flattened orientation with the wafer-like structure, the central layer further having:
        (i) opposing first and second surfaces on either side of the wafer-like structure, wherein the opposing first and second surfaces together sandwich the wafer-like structure and the medial portions of the plurality of embedded fiber bundles, the opposing first surface being adapted to interface with the natural or prosthetic structure and the opposing second surface being adapted to interface with a tissue; and
        (ii) first and second spaced apart openings, each positioned in between the first and second surfaces and positioned proximate at least one edge of the wafer-like structure to allow opposing ends of the plurality of embedded fiber bundles to exit the central layer.

2. The prosthetic anchor of claim 1 further comprising:
    at least one surface membrane configured for cooperating with one of the opposing first and second surfaces of the central layer, the at least one surface membrane providing the interface with at least one of the natural or prosthetic structure or with the tissue.

3. The prosthetic anchor of claim 2 wherein the at least one surface membrane includes a carbon-fiber/epoxy composite, glass-fiber/epoxy composite, or biocompatible metal.

4. The prosthetic anchor of claim 2 wherein the at least one surface membrane is bonded mechanically, adhesively, or both to the central layer.

5. The prosthetic anchor of claim 1 wherein the central layer includes an elastomeric material.

6. The prosthetic anchor of claim 1 wherein the plurality of embedded fiber bundles define artificial tendons.

7. The prosthetic anchor of claim 2 wherein at least one surface of the at least one surface membrane is textured to permit mechanical bonding with the central layer or adjacent structures.

8. The prosthetic anchor of claim 2 further comprising first and second surface membranes, each of the first and second surface membranes cooperating with one of the opposing first and second surfaces of the central layer.

9. The prosthetic anchor of claim 8 wherein at least one of the surface membranes is adapted to interface with the natural or prosthetic structure.

10. The prosthetic anchor of claim 8 wherein at least one of the surface membranes is adapted to interface with tissue.

11. The prosthetic anchor of claim 8 wherein at least one of the surface membranes includes a surface that is textured.

12. A prosthetic anchor configured to attach a natural structure or prosthetic device to a tissue of a human or an animal comprising:
    a wafer-like central layer having first and second surfaces meeting to form at least one edge;
    a first opening and a second opening positioned in between the first and second surfaces and along the at least one edge;

a plurality of fiber bundles that are concentrically aligned, the fiber bundles having two opposing ends and a medial portion between the two opposing ends, the medial portion being curved to form a generally horseshoe-shaped pattern;

the medial portion of each of the plurality of fiber bundles being embedded within the central layer with the first and second surfaces being on either side of, and together sandwiching, the medial portions; and the two opposing ends of each of the plurality of fiber bundles extending through the first and second openings to exit the central layer from the at least one edge.

13. The prosthetic anchor of claim 12 further comprising:
a plurality of pathways extending concentrically through the central layer and in between the first and second surfaces, each of the plurality of pathways receiving at least one of the medial portions of the plurality of fiber bundles and being concentric with another one of the plurality of pathways.

14. The prosthetic anchor of claim 12 further comprising:
a surface membrane configured to cooperate with at least one of the first and second surfaces and to provide an interface between the central layer and the natural structure or prosthetic device or a proximate tissue of the human or the animal.

15. A prosthetic anchor adapted for attachment to a hard outer surface of a natural or prosthetic structure within a human or animal and configured to minimize material stress concentration and minimizing a height of the anchor beyond the outer surface of the structure, the prosthetic anchor comprising:

first and second opposing surfaces, wherein one of the first and second opposing surfaces is configured to conform to the outer surface of the structure;

a wafer-like central layer occupying a space between the first and second opposing surfaces;

first and second openings located proximate at least one edge of the wafer-like central layer; and a plurality of fibers having a medial portion, the medial portion being generally horseshoe-shaped, embedded within the wafer-like central layer, conforming to one of the first and second opposing surfaces, and extending between the first and second openings, wherein a cross-section of the plurality of fibers having a width dimension that is greater than a height dimension.

16. The prosthetic anchor of claim 15, wherein the one of the first and second opposing surfaces is the first opposing surface, the prosthetic further comprising:
a surface membrane configured to be coupled to the first opposing surface and between the first opposing surface and the natural or prosthetic structure.

17. The prosthetic anchor of claim 15, further comprising:
a surface membrane configured to be coupled to at least one of the first and second opposing surfaces.

* * * * *